(12) United States Patent
Ihara

(10) Patent No.: US 7,342,031 B2
(45) Date of Patent: Mar. 11, 2008

(54) THIADIAZOLE COMPOUND AND USE THEREOF

(75) Inventor: Hideki Ihara, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 523 days.

(21) Appl. No.: 10/528,398

(22) PCT Filed: Oct. 7, 2003

(86) PCT No.: PCT/JP03/12831

§ 371 (c)(1),
(2), (4) Date: Mar. 17, 2005

(87) PCT Pub. No.: WO2004/033452

PCT Pub. Date: Apr. 22, 2004

(65) Prior Publication Data

US 2006/0014962 A1    Jan. 19, 2006

(30) Foreign Application Priority Data

Oct. 11, 2002    (JP) .............................. 2002-298489

(51) Int. Cl.
*A01N 43/82* (2006.01)
*C07D 285/08* (2006.01)
*C07D 417/12* (2006.01)

(52) U.S. Cl. ...................... 514/361; 548/125; 548/128; 548/129; 548/130

(58) Field of Classification Search ............... 548/125, 548/128, 129, 130; 514/361
See application file for complete search history.

(56) References Cited

U.S. PATENT DOCUMENTS

| 4,756,741 A | * | 7/1988 | Forster et al. | ............... 504/263 |
| 5,101,034 A | * | 3/1992 | Schmidt et al. | ............. 548/136 |
| 5,827,800 A | * | 10/1998 | Forster et al. | ............... 504/262 |
| 6,544,931 B1 | * | 4/2003 | Muller et al. | ................ 504/262 |

FOREIGN PATENT DOCUMENTS

| DE | 30 30 661 A1 | 4/1982 |
| EP | 1 475 374 A1 | 11/2004 |
| JP | 6 329649 A | 11/1994 |
| WO | WO 92/16527 A1 | 10/1992 |

* cited by examiner

*Primary Examiner*—Golam M. M. Shameem
(74) *Attorney, Agent, or Firm*—Panitch Schwarze Belisario & Nadel LLP

(57) ABSTRACT

The thiadiazole compound represented by the formula (A):

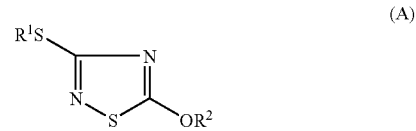

(A)

wherein $R^1$ represents a C1-C7 alkyl group, a C3-C7 alkenyl group, a C3-C7 alkynyl group and the like; R2 represents a C1-C4 alkyl group substituted with a hetero ring group in which the hetero ring group may be substituted, which the hetero ring group is a five-membered ring containing only an oxygen atom(s) or a sulfur atom(s) as a hetero atom(s); has an excellent arthropod pests controlling activity.

10 Claims, No Drawings

THIADIAZOLE COMPOUND AND USE THEREOF

CROSS-REFERENCE TO RELATED APPLICATIONS

This application is a section 371 of International Application No. PCT/JP2003/012831, filed Oct. 7, 2003, which was published in the Japanese language on Apr. 22, 2004, under International Publication No. WO 2004/033452 A1.

FIELD OF THE INVENTION

The present invention relates to a thiadiazole compound and use thereof.

BACKGROUND ARTS

It is known that a kind of thiadiazole compound can be used as an active ingredient of a arthropod pests controlling composition (DE3030661 publication).

However, the arthropod pests controlling activity of this thiadiazole compound is not always enough, then it is desired new compounds having more efficient arthropod pests controlling activity.

DISCLOSURE OF THE INVENTION

The present inventor has earnestly studied, and as a result, found out that the thiadiazole compounds shown by the formula (A) described below have an excellent arthropod pests controlling activity, thereby completing the present invention.

Namely, the present invention relates to a thiadiazole compound shown by the formula (A) (hereinafter, referred as the compound of the present invention):

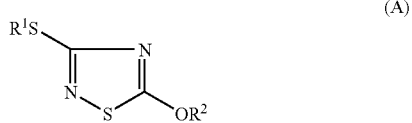

(A)

wherein, in the formula,
$R^1$ represents a C1-C7 alkyl group, a C3-C7 alkenyl group, a C3-C7 alkynyl group, a C2-C7 alkoxyalkyl group, a C2-C7 alkylthioalkyl group, a C4-C7 alkoxyalkoxyalkyl group, a C4-C7 alkylthioalkoxyalkyl group, a phenyl group in which the phenyl group may be substituted, a C1-C2 alkyl group substituted with a phenyl group in which the phenyl group may be substituted, a C1-C2 alkyl group substituted with a phenoxy group in which the phenoxy group may be substituted, a C2-C3 alkoxyalkyl group substituted with a phenyl group in which the phenyl group may be substituted, or the formula (B):

(B)

wherein $R^3$ represents a C1-C3 alkyl group, $R^4$ represents a hydrogen atom, a methyl group, an ethyl group, a propyl group, or a phenyl group in which the phenyl group may be substituted; and $R^2$ represents a C1-C4 alkyl group substituted with a hetero ring group in which the hetero ring group may be substituted, which the hetero ring group is a five-membered ring containing only an oxygen atom(s) or a sulfur atom(s) as a hetero atom(s); a arthropod pests controlling composition comprising the compound of the present invention as an active ingredient, and a method for controlling arthropod pests comprising applying an effective amount of the compound of the present invention to arthropod pests or habitat arthropod pests.

In the compound of the present invention, each of the substituent shown by $R^1$ or $R^2$ is specifically exemplified below.

The C1-C7 alkyl group represented by $R^1$ includes, for example, methyl group, ethyl group, propyl group, isopropyl group, butyl group, sec-butyl group and tert-butyl group.

The C3-C7 alkenyl group represented by $R^1$ includes, for example, allylgroup, 2-butenylgroup, 3-methyl-2-butenyl-group and 2-pentenyl group.

The C3-C7 alkynyl group represented by $R^1$ includes, for example, 2-propynyl group, 1-methyl-2-propynyl group, 2-butynyl group, 3-butynyl group, and 2-pentynyl group.

The C2-C7 alkoxyalkyl group represented by $R^1$ includes, for example, (C1-C6 alkoxy) methyl group; more specifically, methoxymethyl group, ethoxymethyl group, propoxymethyl group and isopropoxymethyl group.

The C2-C7 alkylthioalkyl group represented by $R^1$ includes, for example, (C1-C6 alkylthio) alkyl group; more specifically, methylthiomethyl group, ethylthiomethyl group, propothiomethyl group and isopropylthiomethyl group.

The C4-C7 alkoxyalkoxyalkyl group represented by $R^1$ includes, for example, methoxyethoxymethyl group.

The C4-C7 alkylthioalkoxyalkyl group represented by $R^1$ includes, for example, ethylthioethoxymethyl group.

The phenyl group, in which the phenyl group may be substituted, represented by $R^1$ includes, for example, the phenyl group in which the phenyl group may be substituted with one or more selected from the group consisting of C1-C4 alkyl group (methyl group, ethyl group, propyl group, isopropyl group, tert-butyl group and the like), C1-C4 haloalkyl group (trifluoromethyl group, difluoromethyl group, pentafluoroethyl group, and the like), C1-C4 alkoxy group (methoxy group, ethoxy group, propxy group, isopropoxy group and the like), C1-C4 alkylthio group (methylthio group, ethylthio group and the like), C1-C2 haloalkoxy group (trifluoromethoxy group, difluoromethoxy group and the like), nitro group, cyano group, and halogen atom (fluorine atom, chlorine atom, bromine atom and the like); more specifically, phenyl group, 2-methylphenyl group, 3-methylphenyl group, 4-methylphenyl group, 2-trifluoromethylphenyl group, 3-trifluoromethylphenyl group, 4-trifluoromethylphenyl group, 2-methoxyphenyl group, 3-methoxyphenyl group, 4-methoxyphenyl group, 2-methylthiophenyl group, 3-methylthiophenyl group, 4-methylthiophenyl group, 2-trifluoromethoxyphenyl group, 3-trifluoromethoxyphenyl group, 4-trifluoromethoxyphenyl group, 2-nitrophenyl group, 3-nitrophenyl group, 4-nitrophenyl group, 2-cyanophenyl group, 3-cyanophenyl group, 4-cyanophenyl group, 2-fluorophenyl group, 3-fluorophenyl group, 4-fluorophenyl group, 3,4-difluorophenyl group, 3,5-difluorophenyl group, 2,6-difluorophenyl group, 2,4-difluorophenyl group, 2-chlorophenyl group, 3-chlorophenyl group, 4-chlorophenyl group, 3,4-dichlorophenyl group, 3,5-dichlorophenyl group, 2,6-dichlorophenyl group, 2,4-dichlorophenyl group, 2-bromophenyl group, 3-bromophenyl group, 4-bromophenyl group, 3,4-dibromophenyl group, 3,5-dibromophenyl group, 2,6-dibromophenyl group and 2,4-dibromophenyl group.

The C1-C2 alkyl group substituted with a phenyl group, in which the phenyl group may be substituted, represented by $R^1$ includes, for example, the C1-C2 alkyl group substituted with a phenyl group in which the phenyl group may be substituted with one or more selected from the group consisting of C1-C4 alkyl group (methyl group, ethyl group, propyl group, isopropyl group, tert-butyl group and the like), C1-C4 haloalkyl group (trifluoromethyl group, difluoromethyl group, pentafluoroethyl group, and the like), C1-C4 alkoxy group (methoxy group, ethoxy group, propxy group, isopropoxy group and the like), C1-C4 alkylthio group (methylthio group, ethylthio group and the like), C1-C2 haloalkoxy group (trifluoromethoxy group, difluoromethoxy group and the like), nitro group, cyano group, and halogen atom (fluorine atom, chlorine atom, bromine atom and the like); more specifically, benzyl group, 2-methylbenzyl group, 3-methylbenzyl group, 4-methylbenzyl group, 2-trifluoromethylbenzyl group, 3-trifluoromethylbenzyl group, 4-trifluoromethylbenzyl group, 2-methoxybenzyl group, 3-methoxybenzyl group, 4-methoxybenzyl group, 2-methylthiobenzyl group, 3-methylthiobenzyl group, 4-methylthiobenzyl group, 2-trifluoromethoxybenzyl group, 3-trifluoromethoxybenzyl group, 4-trifluoromethoxybenzyl group, 2-nitrobenzyl group, 3-nitrobenzyl group, 4-nitrobenzyl group, 2-cyanobenzyl group, 3-cyanobenzyl group, 4-cyanobenzyl group, 2-fluorobenzyl group, 3-fluorobenzyl group, 4-fluorobenzyl group, 3,4-difluorobenzyl group, 3,5-difluorobenzyl group, 2,6-difluorobenzyl group, 2,4-difluorobenzyl group, 2-chlorobenzyl group, 3-chlorobenzyl group, 4-chlorobenzyl group, 3,4-dichlorobenzyl group, 3,5-dichlorobenzyl group, 2,6-dichlorobenzyl group, 2,4-dichlorobenzyl group, 2-bromobenzyl group, 3-bromobenzyl group, 4-bromobenzyl group, 3,4-dibromobenzyl group, 3,5-dibromobenzyl group, 2,6-dibromobenzyl group, 2,4-dibromobenzyl group, 1-phenylethyl group, 1-(2-methylphenyl) ethyl group, 1-(3-methylphenyl) ethyl group, 1-(4-methylphenyl)ethyl group, 1-(2-trifluoromethylphenyl)ethyl group, 1-(3-trifluoromethylphenyl)ethyl group, 1-(4-trifluoromethylphenyl)ethyl group, 1-(2-methoxyphenyl)ethyl group, 1-(3-methoxyphenyl) ethyl group, 1-(4-methoxyphenyl) ethyl group, 1-(2-methylthiophenyl)ethyl group, 1-(3-methylthiophenyl)ethyl group, 1-(4-methylthiophenyl)ethyl group, 1-(2-trifluoromethoxyphenyl)ethyl group, 1-(3-trifluoromethoxyphenyl)ethyl group, 1-(4-trifluoromethoxyphenyl)ethyl group, 1-(2-nitrophenyl)ethyl group, 1-(3-nitrophenyl)ethyl group, 1-(4-nitrophenyl)ethyl group, 1-(2-cyanophenyl)ethyl group, 1-(3-cyanophenyl)ethyl group, 1-(4-cyanophenyl)ethyl group, 1-(2-fluorophenyl)ethyl group, 1-(3-fluorophenyl) ethyl group, 1-(4-fluorophenyl) ethyl group, 1-(3,4-difluorophenyl)ethyl group, 1-(3,5-difluorophenyl)ethyl group, 1-(2,6-difluorophenyl)ethyl group, 1-(2,4-difluorophenyl)ethyl group, 1-(2-chlorophenyl)ethyl group, 1-(3-chlorophenyl)ethyl group, 1-(4-chlorophenyl) ethyl group, 1-(3,4-dichlorophenyl)ethyl group, 1-(3,5-dichlorophenyl)ethyl group, 1-(2,6-dichlorophenyl)ethyl group, 1-(2,4-dichlorophenyl)ethyl group, 1-(2-bromophenyl)ethyl group, 1-(3-bromophenyl)ethyl group, 1-(4-bromophenyl)ethyl group, 1-(3,4-dibromophenyl)ethyl group, 1-(3,5-dibromophenyl)ethyl group, 1-(2,6-dibromophenyl) ethyl group, 1-(2,4-dibromophenyl)ethyl group, 2-phenylethyl group, 2-(2-methylphenyl)ethyl group, 2-(3-methylphenyl)ethyl group, 2-(4-methylphenyl)ethyl group, 2-(2-trifluoromethylphenyl)ethyl group, 2-(3-trifluoromethylphenyl)ethyl group, 2-(4-trifluoromethylphenyl)ethyl group, 2-(2-methoxyphenyl) ethyl group, 2-(3-methoxyphenyl)ethyl group, 2-(4-methoxyphenyl)ethyl group, 2-(2-methylthiophenyl)ethyl group, 2-(3-methylthiophenyl)ethyl group, 2-(4-methylthiophenyl)ethyl group, 2-(2-trifluoromethoxyphenyl)ethyl group, 2-(3-trifluoromethoxyphenyl)ethyl group, 2-(4-trifluoromethoxyphenyl)ethyl group, 2-(2-nitrophenyl) ethyl group, 2-(3-nitrophenyl)ethyl group, 2-(4-nitrophenyl) ethyl group, 2-(2-cyanophenyl)ethyl group, 2-(3-cyanophenyl) ethyl group, 2-(4-cyanophenyl)ethyl group, 2-(2-fluorophenyl)ethyl group, 2-(3-fluorophenyl)ethyl group, 2-(4-fluorophenyl)ethyl group, 2-(3,4-difluorophenyl)ethyl group, 2-(3,5-difluorophenyl)ethyl group, 2-(2,6-difluorophenyl) ethyl group, 2-(2,4-difluorophenyl)ethyl group, 2-(2-chlorophenyl)ethyl group, 2-(3-chlorophenyl)ethyl group, 2-(4-chlorophenyl)ethyl group, 2-(3,4-dichlorophenyl)ethyl group, 2-(3,5-dichlorophenyl)ethyl group, 2-(2,6-dichlorophenyl)ethyl group, 2-(2,4-dichlorophenyl)ethyl group, 2-(2-bromophenyl)ethyl group, 2-(3-bromophenyl)ethyl group, 2-(4-bromophenyl)ethyl group, 2-(3,4-dibromophenyl)ethyl group, 2-(3,5-dibromophenyl)ethyl group, 2-(2,6-dibromophenyl)ethyl and 2-(2,4-dibromophenyl)ethyl group.

The C1-C2 alkyl group substituted with a phenyloxy group, in which the phenyloxy group may be substituted, represented by $R^1$ includes, for example, the C1-C2 alkyl group substituted with a phenyloxy group in which the phenyloxy group may be substituted with one or more selected from the group consisting of C1-C4 alkyl group (methyl group, ethyl group, propyl group, isopropyl group, tert-butyl group and the like), C1-C4 haloalkyl group (trifluoromethyl group, difluoromethyl group, pentafluoroethyl group, and the like), C1-C4 alkoxy group (methoxy group, ethoxy group, propxy group, isopropoxy group and the like), C1-C4 alkylthio group (methylthio group, ethylthio group and the like), C1-C2 haloalkoxy group (trifluoromethoxy group, difluoromethoxy group and the like), nitro group, cyano group, and halogen atom (fluorine atom, chlorine atom, bromine atom and the like); more specifically, phenyloxymethyl group, 1-(phenyloxy) ethyl group, 2-(phenyloxy)ethyl group, (2-methylphenyl)oxymethyl group, (3-methylphenyl)oxymethyl group, (4-methylphenyl)oxymethyl group, (2-trifluoromethylphenyl)oxymethyl group, (3-trifluoromethylphenyl)oxymethyl group, (4-trifluoromethylphenyl)oxymethyl group, (2-methoxyphenyl)oxymethyl group, (3-methoxyphenyl)oxymethyl group, (4-methoxyphenyl)oxymethyl group, (2-methylthiophenyl)oxymethyl group, (3-methylthiophenyl)oxymethyl group, (4-methylthiophenyl)oxymethyl group, (2-trifluoromethoxyphenyl)oxymethyl group, (3-trifluoromethoxyphenyl)oxymethyl group, (4-trifluoromethoxyphenyl)oxymethyl group, (2-nitrophenyl) oxymethyl group, (3-nitrophenyl) oxymethyl group, (4-nitrophenyl) oxymethyl group, (2-cyanophenyl) oxymethyl group, (3-cyanophenyl) oxymethyl group, (4-cyanophenyl) oxymethyl group, (2-fluorophenyl) oxymethyl group, (3-fluorophenyl)oxymethyl group, (4-fluorophenyl)oxymethyl group, (3,4-difluorophenyl) oxymethyl group, (3,5-difluorophenyl)oxymethyl group, (2,6-difluorophenyl)oxymethyl group, (2,4-difluorophenyl) oxymethyl group, (2-chlorophenyl)oxymethyl group, (3-chlorophenyl)oxymethyl group, (4-chlorophenyl)oxymethyl group, (3,4-dichlorophenyl)oxymethyl group, (3,5-dichlorophenyl)oxymethyl group, (2,6-dichlorophenyl) oxymethyl group, (2,4-dichlorophenyl)oxymethyl group, (2-bromophenyl)oxymethyl group, (3-bromophenyl)oxymethyl group, (4-bromophenyl)oxymethyl group, (3,4-dibromophenyl)oxymethyl group, (3,5-dibromophenyl)oxymethyl group, (2,6-dibromophenyl)oxymethyl group and (2,4-dibromophenyl)oxymethyl group.

The C2-C3 alkoxyalkyl group substituted with a phenyl group, in which the phenyl group may be substituted, represented by $R^1$ includes, for example, a methoxymethyl group substituted with a phenyl group in which the phenyl group may be substituted with one or more selected from the group consisting of C1-C4 alkyl group (methyl group, ethyl group, propyl group, isopropyl group, tert-butyl group and the like), C1-C4 haloalkyl group (trifluoromethyl group, difluoromethyl group, pentafluoroethyl group, and the like), C1-C4 alkoxy group (methoxy group, ethoxy group, propxy group, isopropoxy group and the like), C1-C4 alkylthio group (methylthio group, ethylthio group and the like), C1-C2 haloalkoxy group (trifluoromethoxy group, difluoromethoxy group and the like), nitro group, cyano group, and halogen atom (fluorine atom, chlorine atom, bromine atom and the like); more specifically, benzyloxymethyl group, (2-methylbenzyl)oxymethyl group, (3-methylbenzyl)oxymethyl group, (4-methylbenzyl)oxymethyl group, (2-trifluoromethylbenzyl)oxymethyl group, (3-trifluoromethylbenzyl)oxymethyl group, (4-trifluoromethylbenzyl)oxymethyl group, (2-methoxybenzyl)oxymethyl group, (3-methoxybenzyl)oxymethyl group, (4-methoxybenzyl)oxymethyl group, (2-methylthiobenzyl)oxymethyl group, (3-methylthiobenzyl)oxymethyl group, (4-methylthiobenzyl)oxymethyl group, (2-trifluoromethoxybenzyl)oxymethyl group, (3-trifluoromethoxybenzyl)oxymethyl group, (4-trifluoromethoxybenzyl)oxymethyl group, (2-nitrobenzyl) oxymethyl group, (3-nitrobenzyl)oxymethyl group, (4-nitrobenzyl)oxymethyl group, (2-cyanobenzyl)oxymethyl group, (3-cyanobenzyl)oxymethyl group, (4-cyanobenzyl)oxymethyl group, (2-fluorobenzyl)oxymethyl group, (3-fluorobenzyl)oxymethyl group, (4-fluorobenzyl)oxymethyl group, (3,4-difluorobenzyl)oxymethyl group, (3,5-difluorobenzyl)oxymethyl group, (2,6-difluorobenzyl)oxymethyl group, (2,4-difluorobenzyl)oxymethyl group, (2-chlorobenzyl)oxymethyl group, (3-chlorobenzyl)oxymethyl group, (4-chlorobenzyl)oxymethyl group, (3,4-dichlorobenzyl)oxymethyl group, (3,5-dichlorobenzyl)oxymethyl group, (2,6-dichlorobenzyl)oxymethyl group, (2,4-dichlorobenzyl)oxymethyl group, (2-bromobenzyl)oxymethyl group, (3-bromobenzyl)oxymethyl group, (4-bromobenzyl)oxymethyl group, (3,4-dibromobenzyl)oxymethyl group, (3,5-dibromobenzyl)oxymethyl group, (2,6-dibromobenzyl)oxymethyl group, (2,4-dibromobenzyl) oxymethyl group.

The formula (B) represented by $R^1$ includes, for example, $R^3$ is a C1-C3 alkyl group and $R^4$ is a hydrogen atom or a phenyl group in which the phenyl group may be substituted with one or more selected from the group consisting of C1-C4 alkyl group (methyl group, ethyl group, propyl group, isopropyl group, tert-butyl group and the like), C1-C4 haloalkyl group (trifluoromethyl group, difluoromethyl group, pentafluoroethyl group, and the like), C1-C4 alkoxy group (methoxy group, ethoxy group, propxy group, isopropoxy group and the like), C1-C4 alkylthio group (methylthio group, ethylthio group and the like), C1-C2 haloalkoxy group (trifluoromethoxy group, difluoromethoxy group and the like), nitro group, cyano group, and halogen atom (fluorine atom, chlorine atom, bromine atom and the like); more specifically, acetoxy methyl group and α-acetyloxybenzyl group.

The C1-C4 alkyl group substituted with a hetero ring group (hereinafter, the hetero ring group is referred as the present hetero ring group) in which the hetero ring group may be substituted, which the hetero ring group is a five-membered ring containing only an oxygen atom(s) or a sulfur atom(s) as a hetero atom(s), represented by $R^2$ includes, for example, a C1-C4 alkyl group substituted with the present hetero ring group in which the present hetero ring group may be substituted with one or more selected from the group consisting of C1-C4 alkyl group (methyl group, ethyl group, propyl group, isopropyl group, tert-butyl group and the like), halogen atom (fluorine atom, chlorine atom, bromine atom and the like), trifluoromethyl group, formyl group and nitro group; more specifically, a methyl group substituted with the present hetero ring group in which the present hetero ring group may be substituted with one or more selected from the group consisting of halogen atom (fluorine atom, chlorine atom, bromine atom and the like), C1-C4 alkyl group (methyl group, ethyl group, propyl group, isopropyl group, tert-butyl group and the like), trifluoromethyl group, formyl group and nitro group, and an ethyl group substituted with the present hetero ring group at 1-position of ethyl group in which the present hetero ring group may be substituted with one or more selected from the group consisting of C1-C4 alkyl group (methyl group, ethyl group, propyl group, isopropyl group, tert-butyl group and the like), halogen atom (fluorine atom, chlorine atom, bromine atom and the like), trifluoromethyl group, formyl group and nitro group.

In the C1-C4 alkyl group substituted with the present hetero ring group represented by $R^2$, the present hetero ring group includes, for example, a five membered ring group which contains only an oxygen atom(s) as a hetero atom(s), a five membered saturated ring group which contains only an oxygen atom(s) as a hetero atom(s), a five membered saturated ring group which contains only two oxygen atoms as hetero atoms, a five membered ring group which contains only an oxygen atom as a hetero atom, a five membered ring group which contains only a sulfur atom(s) as a hetero atom(s).

The mode of the C1-C4 alkyl group substituted with the present hetero ring which the present hetero ring may be substituted represented by $R^2$ includes, for example, groups described by the formula (1) to (10) shown below.

the formula (1):

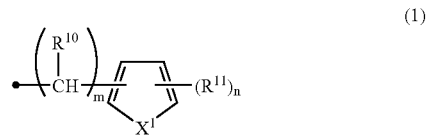

(1)

wherein, in the formula, $R^{10}$ represents a hydrogen atom or a methyl group, $R^{11}$ represents a halogen atom, a C1-C4 alkyl group, a trifluoromethyl group, a formyl group, or a nitro group, $X^1$ represents an oxygen atom or a sulfur atom, m represents 1 or 2, n represents an integer of 0 to 3. In case of n is an integer of 2 or more, each of $R^{11}$s may be same or different;

the formula (2):

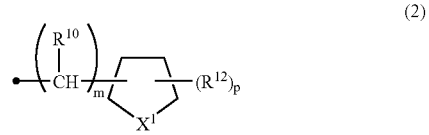

(2)

wherein, in the formula, $R^{10}$ represents a hydrogen atom or a methyl group, $R^{12}$ represents a C1-C4 alkyl group, $X^1$ represents an oxygen atom or a sulfur atom, m represents 1 or 2, p represents an integer of 0 to 7. In case of p is an integer of 2 or more, each of $R^{12}$s may be same or different;

the formula (3):

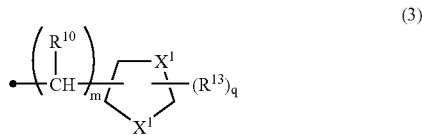

(3)

wherein, in the formula, $R^{10}$ represents a hydrogen atom or a methyl group, $R^{13}$ represents a C1-C4 alkyl group, $X^1$ represents an oxygen atom or a sulfur atom, m represents 1 or 2, q represents an integer of 0 to 5. In case of q is an integer of 2 or more, each of $R^{13}$s may be same or different;

the formula (4):

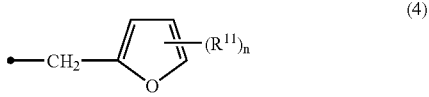

(4)

wherein, in the formula, $R^{11}$ represents a halogen atom, a C1-C4 alkyl group, a trifluoromethyl group, a formyl group or a nitro group, n represents an integer of 0 to 3. In case of an integer of 2 or more, each of $R^{11}$s may be same or different;

the formula (5):

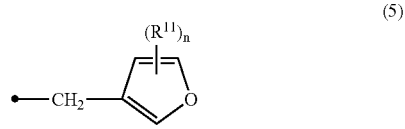

(5)

wherein, in the formula, $R^{11}$ represents a halogen atom, a C1-C4 alkyl group, a trifluoromethyl group, a formyl group or a nitro group, n represents an integer of 0 to 3. In case of an integer of 2 or more, each of $R^{11}$s may be same or different;

the formula (6):

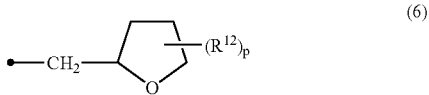

(6)

wherein, in the formula, $R^{12}$ represents a C1-C4 alkyl group, p represents an integer of 0 to 7. In case of p is an integer of 2 or more, each of $R^{12}$s may be same or different;

the formula (7):

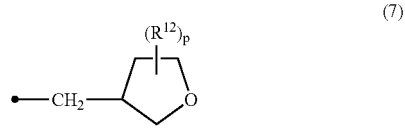

(7)

wherein, in the formula, $R^{12}$ represents a C1-C4 alkyl group, p represents an integer of 0 to 7. In case of p is an integer of 2 or more, each of $R^{12}$s may be same or different;

the formula (8):

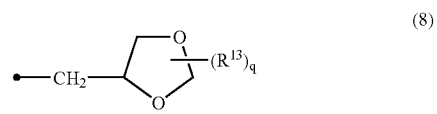

(8)

wherein, in the formula, $R^{13}$ represents a C1-C4 alkyl group, q represents an integer of 0 to 5. In case of q is an integer of 2 or more, each of $R^{13}$s may be same or different;

the formula (9):

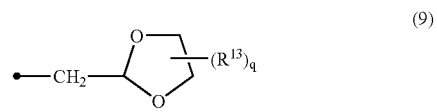

(9)

wherein, in the formula, $R^{13}$ represents a C1-C4 alkyl group, q represents an integer of 0 to 5. In case of q is an integer of 2 or more, each of $R^{13}$s may be same or different;

the formula (10):

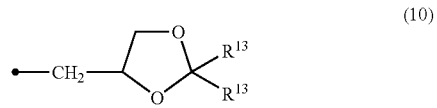

(10)

wherein, in the formula, $R^{13}$ represents a C1-C4 alkyl group, two $R^{13}$'s are the same or different from each other.

Embodiments of the compound of the present invention include, for example, the following compounds:

the thiadiazole compound wherein $R^1$ is a C1-C7 alkyl group in the formula (A);

the thiadiazole compound wherein $R^1$ is a C3-C7 alkenyl group, a C2-C7 alkoxyalkyl group, a C2-C7 alkylthioalkyl group, C4-C7 alkoxyalkoxyalkyl group or C4-C7 alkylthioalkoxyalkyl group in the formula (A);

the thiadiazole compound wherein $R^1$ is a phenyl group in which the phenyl group may be substituted with one or more selected from the Substituent Group A, a C1-C2 alkyl group substituted with a phenyl group in which the phenyl group may be substituted with one or more selected from the Substituent Group A, a C1-C2 alkyl group substituted with a phenyloxy group in which the phenyloxy group may be substituted with one or more selected from the Substituent Group A or a C2-C3 alkoxyalkyl group substituted with a phenyl group in which the phenyl group may be substituted with one or more selected from the Substituent Group A, Substituent Group A C1-C4 alkyl group, C1-C4 haloalkyl group, C1-C4 alkoxy group, C1-C4 alkylthio group, C1-C4 haloalkoxy group, nitro group, cyano group, and halogen atoms, in the formula (A);

the thiadiazole compound wherein $R^1$ is a group designated by formula (B):

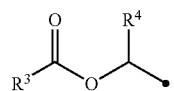

(B)

wherein, in the formula, $R^3$ represents a C1-C3 alkyl group, $R^4$ represents a hydrogen atom, a methyl group, an ethyl group, or a phenyl group optionally substituted with one or more selected from C1-C4 alkyl group, C1-C4 haloalkyl group, C1-C4 alkoxy group, C1-C4 alkylthio group, C1-C4 haloalkoxy group, nitro group, cyano group and halogen atoms,
in the formula (A);
the thiadiazole compound wherein $R^1$ is a phenyl group optionally substituted with one or more selected from the Substituent Group A, a benzyl group optionally substituted with one or more selected from the Substituent Group A, phenyloxymethyl group optionally substituted with one or more selected from the Substituent Group A or benzyloxymethyl group optionally substituted with one or more selected from the Substituent Group A in the formula (A);
the thiadiazole compound wherein $R^2$ is a group designated by the formula (1):

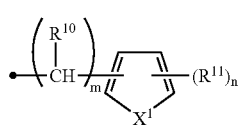

(1)

wherein, in the formula, $R^{10}$ represents a hydrogen atom or a methyl group, $R^{11}$ represents a halogen atom, a C1-C4 alkyl group, a trifluoromethyl group, a formyl group or a nitro group, $X^1$ represents an oxygen atom or a sulfur atom, m represents 1 or 2, n represents an integer of 0 to 3, in case of n is an integer of 2 or more, each of $R^{11}$s may be same or different,
a group designated by the formula (2):

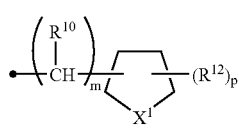

(2)

wherein, in the formula, $R^{10}$ represents a hydrogen atom or a methyl group, $R^{12}$ represents a C1-C4 alkyl group, $X^1$ represents an oxygen atom or a sulfur atom, m represents 1 or 2, p represents an integer of 0 to 7, in case of p is an integer of 2 or more, each of $R^{12}$s may be same or different, or a group designated by the formula (3):

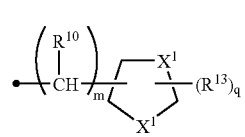

(3)

wherein, in the formula, $R^{10}$ represents a hydrogen atom or a methyl group, $R^{13}$ represents a C1-C4 alkyl group, $X^1$ represents an oxygen atom or a sulfur atom, m represents 1 or 2, q represents an integer of 0 to 5, in case of q is an integer of 2 or more, each of $R^{13}$s may be same or different in the formula (A);
the thiadiazole compound wherein $R^1$ is a group designated by the formula (4):

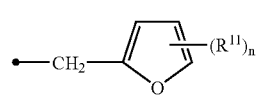

(4)

wherein, in the formula, $R^{11}$ represents a halogen atom, a C1-C4 alkyl group, a trifluoromethyl group, a formyl group and a nitro group, n represents an integer of 0 to 3, in case of n is an integer of 2 or more, each of $R^{11}$s may be same or different,
a group designated by the formula (5):

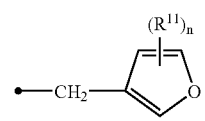

(5)

wherein, in the formula, $R^{11}$ represents a halogen atom, a C1-C4 alkyl group, a trifluoromethyl group, a formyl group and a nitro group, n represents an integer of 0 to 3, in case of n is an integer of 2 or more, each of $R^{11}$s may be same or different,
a group designated by the formula (6):

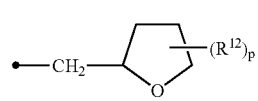

(6)

wherein, in the formula, $R^{12}$ represents a C1-C4 alkyl group, p represents an integer of 0 to 7, in case of p is an integer of 2 or more, each of $R^{12}$s may be same or different,
a group designated by the formula (7):

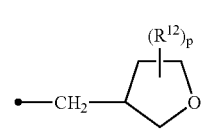

(7)

wherein, in the formula, $R^{12}$ represents a C1-C4 alkyl group, p represents an integer of 0 to 7, in case of p is an integer of 2 or more, each of $R^{12}$s may be same or different, a group designated by the formula (8):

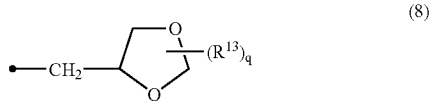

(8)

wherein, in the formula, $R^{13}$ represents a C1-C4 alkyl group, q represents an integer of 0 to 5, in case of q is an integer of 2 or more, each of $R^{13}$s may be same or different, a group designated by the formula (9):

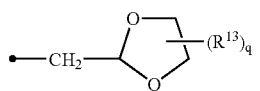

(9)

wherein, in the formula, $R^{13}$ represents a C1-C4 alkyl group, q represents an integer of 0 to 5, in case of q is an integer of 2 or more, each of $R^{13}$s may be same or different, or a group designated by the formula (10):

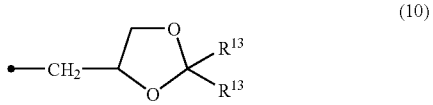

(10)

wherein, in the formula, $R^{13}$ represents a C1-C4 alkyl group, two $R^{13}$s are the same or different from each other.

The following will describe a production process for the compound of the present invention.

In the compound of the present invention, the compound wherein $R^1$ represents a C1-C7 alkyl group, a C3-C7 alkenyl group, a C3-C7 alkynyl group, a C2-C7 alkoxyalkyl group, a C2-C7 alkylthioalkyl group, a C4-C7 alkoxyalkoxyalkyl group, a C4-C7 alkylthioalkoxyalkyl group, a phenyl group in which the phenyl group may be substituted, a phenyl C1-C2 alkyl group in which the phenyl may be substituted, a phenyloxy C1-C2 alkyl group in which the phenyloxy may be substituted or a phenyl C2-C3 alkoxyalkyl group in which the phenyl may be substituted, namely the compound shown by the formula (A-1), can be produced, for example, by making a 5-chloro-1,2-tiadiazole compound shown by the formula (I) react with an alcohol compound shown by the formula (II).

-continued

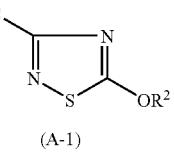

(A-1)

wherein, in the formula, $R^{1-1}$ represents a C1-C7 alkyl group, a C3-C7 alkenyl group, a C3-C7 alkynyl group, a C2-C7 alkoxyalkyl group, a C2-C7 alkylthioalkyl group, a C4-C7 alkoxyalkoxyalkyl group, a C4-C7 alkylthioalkoxyalkyl group, a phenyl group in which the phenyl group may be substituted, a phenyl C1-C2 alkyl group in which the phenyl may be substituted, a phenyloxy C1-C2 alkyl group in which the phenyloxy may be substituted or a phenyl C2-C3 alkoxyalkyl group in which the phenyl may be substituted; $R^2$ has a same meaning as described above.

The reaction is usually carried out in the presence of a base, usually in a solvent.

The solvent to be used to the reaction includes, for example, aliphatic hydrocarbons such as hexane, heptane, octane and the like; aromatic hydrocarbons such as toluene, xylene and the like; ethers such as tetrahydrofuran, 1,4-dioxane, methyl-tert-butylether, 1,2-dimethoyethane and the like; N,N-dimethylformamide, and the mixture thereof.

The base to be used to the reaction includes, for example, carbonates such as potassium carbonate, sodium carbonate and the like, and the mixture thereof.

Concerning to the amount of the reagent to be used to the reaction, the amount of the alcohol compound shown by the formula (II) is usually 1 to 1.5 moles relative to 1 mole of the 5-chloro-1,2-tiadiazole compound shown by the formula (I), the amount of the base is 1 to 1.5 moles relative to the alcohol compound shown by the formula (II).

The reaction temperature is usually in the range of −20 to 80° C., and the reaction time is usually in the range of 0.5 to 24 hours.

After completion of the reaction, the compound of the present invention shown by the formula (A-1) can be islated by subjecting the reaction mixture to post-treatment such as adding the reaction mixture into water, extracting with anorganic solvent, drying and consentrating the extract and the like. The islated compound of the present invention shown by the formula (A-1) can be purified by a techniqe such as chromatography, recrystallization and the like, if necessary.

In the compound of the present invention, the compound wherein $R^1$ represents the group shown by the formula (B), namely the compound shown by the formula (A-2), can be produced by, for example, by making the thiadiazole compound shown by the formula (III) react with oxidizing agent (hereinafter, referred as the first half step), after that, making the product of the first half step react with acid anhydride shown by the formula (V) (hereinafter, referred as the later half step).

-continued

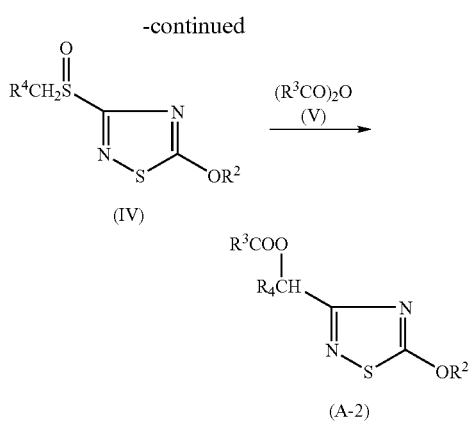

wherein, in the formula, $R^2$, $R^3$ and $R^4$ have same meanings as described above.

(The First Half Step)

The reaction of the first half step is usually carried out in a solvent. The solvent to be used to the reaction includes, for example, halogenated aliphatic hydrocarbons such as dichloromethane, chloroform and the like and water.

The oxidizing agent to be used to the reaction includes, for example, peroxy acids such as 3-chloroperoxybenzoic acid. The amount of the oxidizing agent to be used to the reaction is usually 1 to 1.5 moles relative to 1 mole of the thiadiazole compound shown by the formula (III).

The reaction temperature is usually in the range of −20 to 30° C., and the reaction time is usually in the range of momentary to 24 hours.

After completion of the reaction, the sulfoxide compound shown by the formula (IV) can be islated by subjecting the reaction mixture to post-treatment such as adding the reaction mixture into water; extracting with an organic solvent; if necessary washing the obtained organic layer with an aquous solution of reductant such as sodium sulfite, sodium thiosulfate and the like, an aquous solution of base (sodium bicarbonate and the like); drying and consentrating the organic layer and the like. The islated the sulfoxide compound shown by the formula (IV) can be purified by a techniqe such as chromatography, recrystallization and the like.

(The Later Half Step)

The later half step can be carried out by making the slufoxide compound shown by the formula (IV) react with the acid anhydride shown by the formula (V).

The reaction is carried out in the presence of a solvent or absence of a solvent, and usually in the presence of a base.

The base to be used to the reaction inclueds, for example, pyridines such as 2,6-lutidine and the like, alkali metal salts of acetic acid such as sodium acetate and the like.

Concerning to the amount of the reagent to be used to the reaction, the amount of the acid anhydride shown by the formula (V) is 1 to 50 moles relative to 1 mole of the sulfoxide compound shown by the formula (IV), the amount of the base is 1 to 10 moles relative to the sulfoxide compound shown by the formula (IV).

The reaction can be carried out in the presence of trifluoroacetic anhydride, if necessary. In this case, the amount of trifluoroacetic anhydride is usually 0.01 to 5 moles relative to 1 mole of the sulfoxide compound shown by the formula (IV).

The reaction temperature is usually in the range of 0 to 150° C., and the reaction time is usually in the range of 1 to 72 hours.

After completion of the reaction, the compound of the present invention shown by the formula (A-2) can be islated by subjecting the reaction mixture to post-treatment such as adding the reaction mixture into aquous solution of a base (ex. sodiumbicarbonate), extracting with an organic solvent, drying and consentrating the obtained organic layer and the like. The islated compound of the present invention shown by the formula (A-2) can be purified by a techniqe such as chromatography, recrystallization and the like, if necessary.

The compound shown by the formula (I) can be produced, for example, by the method described in Chem. Ber. 90, 892(1957).

Next, examples of the present compounds are shown.

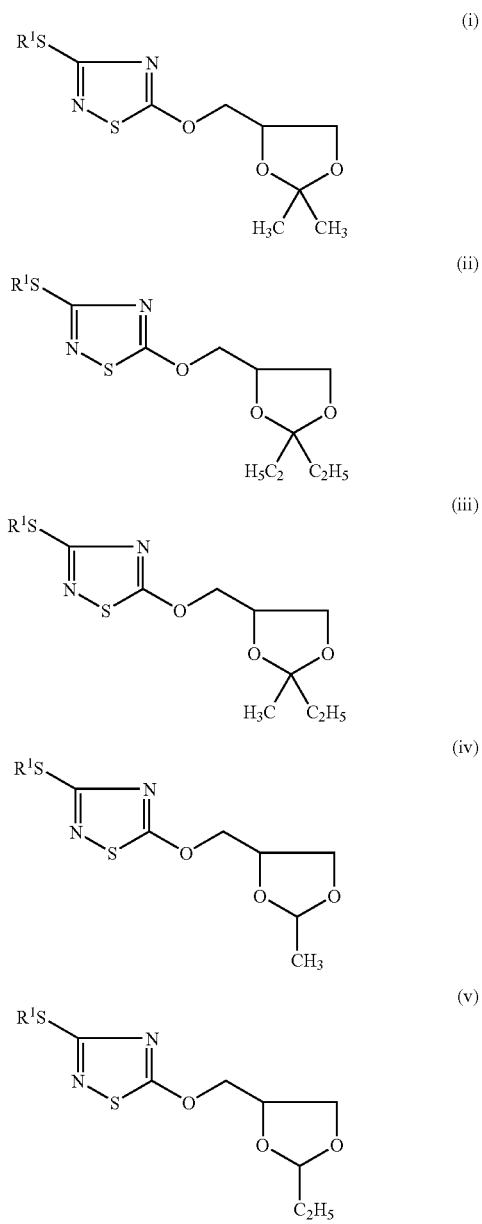

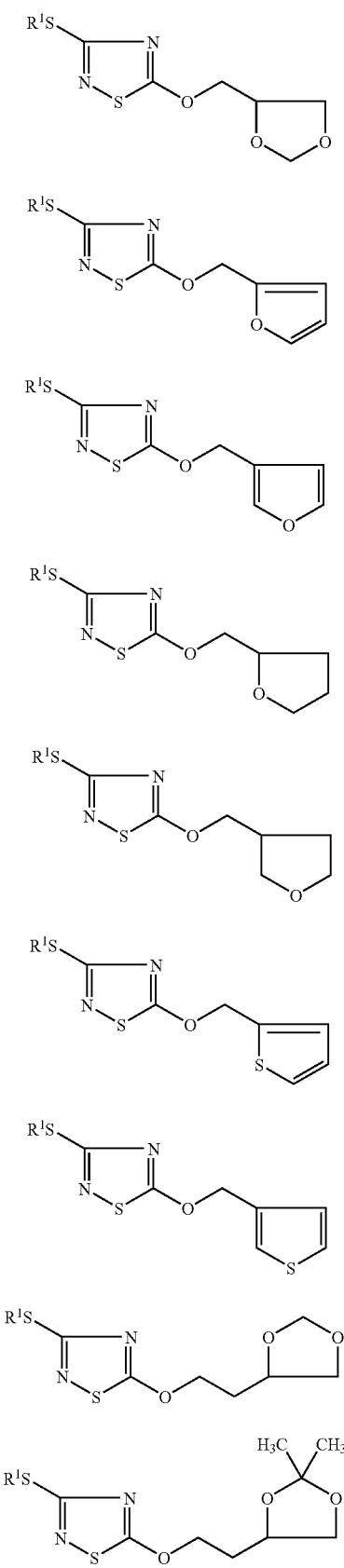
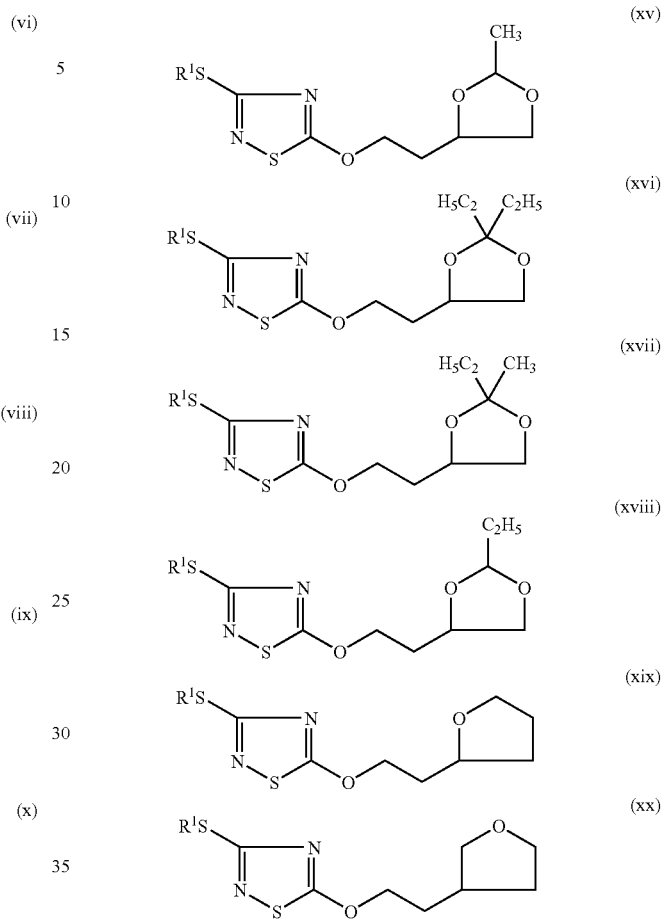

In the formula (i) to the formula (xx), $R^1$ represents one of the group selected from methyl group, ethyl group, propyl group, isopropyl group, butyl group, sec-butyl group, tert-butyl group, allyl group, 2-butenyl group, 3-methyl-2-butenyl group, 2-pentenyl group, 2-propynyl group, 1-methyl-2-propynyl group, 2-butynyl group, 3-butynyl group, 2-pentynyl group, methoxymethyl group, ethoxymethyl group, propoxymethyl group, isopropoxymethyl group, butoxymethyl group, isobutoxymethyl group, sec-butoxymethyl group, tert-butoxymethyl group, methylthiomethyl group, ethylthiomethyl group, propylthiomethyl group, isopropylthiomethyl group, methoxyethoxymethyl group, ethoxyethoxymethyl group, methylthioethoxymethyl group, phenyl group, 2-methylphenyl group, 3-methylphenyl group, 4-methylphenyl group, 2-trifluoromethylphenyl group, 3-trifluoromethylphenyl group, 4-trifluoromethylphenyl group, 2-methoxyphenyl group, 3-methoxyphenyl group, 4-methoxyphenyl group, 2-methylthiophenyl group, 3-methylthiophenyl group, 4-methylthiophenyl group, 2-trifluoromethoxyphenyl group, 3-trifluoromethoxyphenyl group, 4-trifluoromethoxyphenyl group, 2-nitrophenyl group, 3-nitrophenyl group, 4-nitrophenyl group, 2-cyanophenyl group, 3-cyanophenyl group, 4-cyanophenyl group, 2-fluorophenyl group, 3-fluorolphenyl group, 4-fluorophenyl group, 3,4-difluorophenyl group, 3,5-difluorolphenyl group, 2,6-difluorophenyl group, 2,4-difluorophenyl group, 2-chlorophenyl group, 3-chlorophenyl group, 4-chlorophenyl group, 3,4-dichlorophenyl group, 3,5-dichlorophenyl group, 2,6-dichlorophenyl group, 2,4-dichlorophenyl group, 2-bromophenyl group, 3-bromophenyl group, 4-bromophenyl group, 3,4-dibromophenyl group, 3,5-dibromophenyl group, 2,6-dibromophenyl group, 2,4-dibromophenyl group, benzyl group, 2-methylbenzyl group, 3-methylbenzyl group, 4-methylbenzyl group, 2-trifluoromethylbenzyl group, 3-trifluoromethylbenzyl group, 4-trifluoromethylbenzyl group, 2-methoxybenzyl group, 3-methoxybenzyl group, 4-methoxybenzyl group, 2-methythiobenzyl group, 3-methylthiobenzyl group, 4-methylthiobenzyl group, 2-trifluoromethoxybenzyl group, 3-trifluoromethoxybenzyl group, 4-trifluoromethoxybenzyl group, 2-nitrobenzyl group, 3-nitrobenzyl group, 4-nitrobenzyl group, 2-cyanobenzyl group, 3-cyanobenzyl group, 4-cyanobenzyl group, 2-flourobenzyl group, 3-flourobenzyl group, 4-flourobenzyl group, 3,4-diflourobenzyl group, 3,5-diflourobenzyl group, 2,6-diflourobenzyl group, 2,4-diflourobenzyl group, 2-chlorobenzyl group, 3-chlorobenzyl group, 4-chlorobenzyl group, 3,4-dichlorobenzyl group, 3,5-dichlorobenzyl group, 2,6-dichlorobenzyl group, 2,4-dichlorobenzyl group, 2-bromobenzyl group, 3-bromobenzyl group, 4-bromobenzyl group, 3,4-dibromobenzyl group, 3,5-dibromobenzyl group, 2,6-dibromobenzyl group, 2,4-dibromobenzyl group, 1-(phenyl)ethyl group, 1-(2-methylphenyl)ethyl group, 1-(3-methylphenyl)ethyl group, 1-(4-methylphenyl)ethyl group, 1-(2-trifluoromethylphenyl)ethyl group, 1-(3-trifluoromethylphenyl)ethyl group, 1-(4-trifluoromethylphenyl)ethyl group, 1-(2-methoxyphenyl)ethyl group, 1-(3-methoxyphenyl) ethyl group, 1-(4-methoxyphenyl)ethyl group, 1-(2-methylthiophenyl)ethyl group, 1-(3-methylthiophenyl)ethyl group, 1-(4-methylthiophenyl)ethyl group, 1-(2-trifluoromethoxyphenyl)ethyl group, 1-(3-trifluoromethoxyphenyl)ethyl group, 1-(4-trifluoromethoxyphenyl)ethyl group, 1-(2-nitrophenyl)ethyl group, 1-(3-nitrophenyl)ethyl group, 1-(4-nitrophenyl)ethyl group, 1-(2-cyanophenyl)ethyl group, 1-(3-cyanophenyl)ethyl group, 1-(4-cyanophenyl)ethyl group, 1-(2-fluorophenyl)ethyl group, 1-(3-fluorophenyl)ethyl group, 1-(4-fluorophenyl) ethyl group, 1-(3,4-difluorophenyl)ethyl group, 1-(3,5-difluorophenyl)ethyl group, 1-(2,6-difluorophenyl)ethyl group, 1-(2,4-difluorophenyl)ethyl group, 1-(2-chlorophenyl)ethyl group, 1-(3-chlorophenyl)ethyl group, 1-(4-chlorophenyl) ethyl group, 1-(3,4-dichlorophenyl)ethyl group, 1-(3,5-dichlorophenyl)ethyl group, 1-(2,6-dichlorophenyl)ethyl group, 1-(2,4-dichlorophenyl)ethyl group, 1-(2-bromophenyl)ethyl group, 1-(3-bromophenyl) ethyl group, 1-(4-bromophenyl)ethyl group, 1-(3,4-dibromophenyl) ethyl group, 1-(3,5-dibromophenyl) ethyl group, 1-(2,6-dibromophenyl) ethyl group, 1-(2,4-dibromophenyl)ethyl group, 2-(phenyl) ethyl group, 2-(2-methylphenyl)ethyl group, 2-(3-methylphenyl)ethyl group, 2-(4-methylphenyl)ethyl group, 2-(2-trifluoromethylphenyl)ethyl group, 2-(3-trifluoromethylphenyl)ethyl group, 2-(4-trifluoromethylphenyl)ethyl group, 2-(2-methoxyphenyl) ethyl group, 2-(3-methoxyphenyl) ethyl group, 2-(4-methoxyphenyl)ethyl group, 2-(2-methylthiophenyl)ethyl group, 2-(3-methylthiophenyl)ethyl group, 2-(4-methylthiophenyl) ethyl group, 2-(2-trifluoromethoxyphenyl)ethyl group, 2-(3-trifluoromethoxyphenyl)ethyl group, 2-(4-trifluoromethoxyphenyl)ethyl group, 2-(2-nitrophenyl)ethyl group, 2-(3-nitrophenyl)ethyl group, 2-(4-nitrophenyl)ethyl group, 2-(2-cyanophenyl)ethyl group, 2-(3-cyanophenyl)ethyl group, 2-(4-cyanophenyl)ethyl group, 2-(2-fluorophenyl)ethyl group, 2-(3-fluorophenyl)ethyl group, 2-(4-fluorophenyl) ethyl group, 2-(3,4-difluorophenyl)ethyl group, 2-(3,5-difluorophenyl)ethyl group, 2-(2,6-difluorophenyl)ethyl group, 2-(2,4-difluorophenyl)ethyl group, 2-(2-chlorophenyl)ethyl group, 2-(3-chlorophenyl)ethyl group, 2-(4-chlorophenyl) ethyl group, 2-(3,4-dichlorophenyl)ethyl group, 2-(3,5-dichlorophenyl)ethyl group, 2-(2,6-dichlorophenyl)ethyl group, 2-(2,4-dichlorophenyl)ethyl group, 2-(2-bromophenyl)ethyl group, 2-(3-bromophenyl)ethyl group, 2-(4-bromophenyl)ethyl group, 2-(3,4-dibromophenyl) ethyl group, 2-(3,5-dibromophenyl)ethyl group, 2-(2,6-dibromophenyl) ethyl group, 2-(2,4-dibromophenyl)ethyl group, phenyloxymethyl group, 1-(phenyloxy)ethyl group, 2-(phenyloxy) ethyl group, (2-methylphenyl)oxymethyl group, (3-methylphenyl)oxymethyl group, (4-methylphenyl)oxymethyl group, (2-trifluoromethylphenyl)oxymethyl group, (3-trifluoromethylphenyl)oxymethyl group, (4-trifluoromethylphenyl)oxymethyl group, (2-methoxyphenyl)oxymethyl group, (3-methoxphenyl)oxymethyl group, (4-methoxphenyl)oxymethyl group, (2-methythiophenyl)oxymethyl group, (3-methylthiophenyl)oxymethyl group, (4-methylthiophenyl)oxymethyl group, (2-trifluoromethoxyphenyl)oxymethyl group, (3-trifluoromethoxphenyl)oxymethyl group, (4-trifluoromethoxphenyl)oxymethyl group, (2-nitrophenyl)oxymethyl group, (3-nitrophenyl) oxymethyl group, (4-nitrophenyl)oxymethyl group, (2-cyanophenyl)oxymethyl group, (3-cyanophenyl) oxymethyl group, (4-cyanophenyl)oxymethyl group, (2-fluorophenyl)oxymethyl group, (3-fluorophenyl)oxymethyl group, (4-fluorophenyl) oxymethyl group, (3,4-difluorophenyl)oxymethyl group, (3,5-difluorophenyl)oxymethyl group, (2,6-difluorophenyl) oxymethyl group, (2,4-difluorophenyl)oxymethyl group, (2-cholorophenyl)oxymethyl group, (3-cholorophenyl)oxymethyl group, (4-cholorophenyl)oxymethyl group, (3,4-dicholorophenyl)oxymethyl group, (3,5-dicholorophenyl) oxymethyl group, (2,6-dicholorophenyl)oxymethyl group, (2,4-dicholorophenyl)oxymethyl group, (2-bromophenyl) oxymethyl group, (3-bromophenyl) oxymethyl group, (4-bromophenyl)oxymethyl group, (3,4-dibromophenyl) oxymethyl group, (3,5-dibromophenyl)oxymethyl group, (2,6-dibromophenyl)oxymethyl group, (2,4-dibromophenyl) oxymethyl group, benzyloxymethyl group, (2-methylbenzyl)oxymethyl group, (3-methylbenzyl)oxymethyl group, (4-methylbenzyl)oxymethyl group, (2-trifluoromethylbenzyl)oxymethyl group, (3-trifluormethylbenzyl)oxymethyl group, (4-trifluormethylbenzyl)oxymethyl group, (2-methoxybenzyl) oxymethyl group, (3-methoxybenzyl) oxymethyl group, (4-methoxybenzyl)oxymethyl group, (2-methylthiobenzyl)oxymethyl group, (3-methylthiobenzyl) oxymethyl group, (4-methylthiobenzyl)oxymethyl group, (2-trifluoromethoxybenzyl)oxymethyl group, (3-trifluoromethoxybenzyl)oxymethyl group, (4-trifluoromethoxybenzyl)oxymethyl group, (2-nitrobenzyl)oxymethyl group, (3-nitrobenzyl) oxymethyl group, (4-nitrobenzyl)oxymethyl group, (2-cyanobenzyl) oxymethyl group, (3-cyanobenzyl) oxymethyl group, (4-cyanobenzyl)oxymethyl group, (2-fluorobenzyl)oxymethyl group, (3-fluorobenzyl)oxymethyl group, (4-fluorobenzyl)oxymethyl group, (3,4-difluorobenzyl)oxymethyl group, (3,5-difluorobenzyl)oxymethyl group, (2,6-difluorobenzyl)oxymethyl group, (2,4-difluorobenzyl)oxymethyl group, (2-chlorobenzyl)oxymethyl group, (3-chlorobenzyl)oxymethyl group, (4-chlorobenzyl) oxymethyl group, (3,4-dichlorobenzyl)oxymethyl group, (3,5-dichlorobenzyl)oxymethyl group, (2,6-dichlorobenzyl) oxymethyl group, (2,4-dichlorobenzyl)oxymethyl group, (2-bromobenzyl)oxymethyl group, (3-bromobenzyl) oxymethyl group, (4-bromobenzyl)oxymethyl group, (3,4-dibromobenzyl)oxymethyl group, (3,5-dibromobenzyl)oxymethyl group, (2,6-dibromobenzyl)oxymethyl group, (2,4-dibromobenzyl)oxymethyl group, acetyloxymethyl group, propioniloxymethyl group and α-acetoxybenzyl group.

The arthropod pests against which the compound of the present invention has control activity may include insect pests and acarine pests. Specific examples are listed below.

Hemiptera: Delphacidae such as *Laodelphax striatellus*, *Nilaparvata lugens*, and *Sogatella furcifera*; Deltocephalidae such as *Nephotettix cincticeps* and *Empoasca onukii*; Aphididae such as *Aphis gossypii* and *Myzus persicae*;

Pentatomidae; Aleyrodidae such as *Trialeurodes vaporariorum, Bemisia tabaci,* and *Bemisia argentifolii*; Coccidae; Tingidae; Psyllidae;

Lepidoptera: Pyralidae such as *Chilo suppressalis, Cnaphalocrocis medinalis, Ostrinia nubilalis,* and *Parapediasia teterrella*; Noctuidae such as *Spodoptera litura, Spodoptera exigua, Pseudaletia separata, Mamestra brassicae, Agrotis ipsilon, Thoricoplusia* spp., *Heliothis* spp., *Helicoverpa* spp., and *Earias* spp.; Pieridae such as *Pieris rapae crucivora*; Tortricidae such as *Adoxophyes orana fasciata, Grapholita molesta,* and *Cydia pomonella*; Carposinidae such as *Carposina niponensis*; Lyonetiidae such as *Lyonetia clerkella*; Gracillariidae such as *Phyllonorycter ringoniella*; Phyllocnistidae such as *Phyllocnistis citrella*; Yponomeutidae such as *Plutela xylostella*; Gelechiidae such as *Pectinophora gossypiella*; Arctiidae; Tineidae;

Diptera: Calicidae such as *Culex pipiens pallens, Culex tritaeniorhynchus,* and *Culex quinquefasciatus; Aedes* spp. such as *Aedes aegypti* and *Aedes albopictus; Anopheles* spp. such as *Anopheles sinensis*; Chironomidae; Muscidae such as *Musca domestica* and *Muscina stabulans*; Calliphoridae; Sarcophagidae; Fanniidae; Anthomyiidae such as *Delia platura* and *Delia antiqua*; Tephritidae; Drosophilidae; Psychodidae; Tabanidae; Simuliidae; Stomoxyidae; Agromyzidae;

Coleoptera: *Diabrotica* spp. such as *Diabrotica virgifera virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus,* and *Callosobruchuys chienensis*; Tenebrionidae such as *Tenebrio molitor* and *Tribolium castaneum*; Chrysomelidae such as *Oulema oryzae, Aulacophora femoralis, Phyllotreta striolata,* and *Leptinotarsa decemlineata*; Anobiidae; *Epilachna* spp. such as *Epilachna vigintioctopunctata*; Lyctidae; Bostrychidae; Cerambycidae; *Paederus fuscipes*;

Thysanoptera: Thripidae spp. including *Thrips* spp. such as *Thrips palmi, Frankliniella* spp. such as *Frankliniella occidentalis,* and *Sciltothrips* spp. such as *Sciltothrips dorsalis*; Phlaeothripidae spp.;

Hymenoptera: Tenthredimidae; Formicidae; Vespidae;

Dictyoptera: *Periplaneta* spp.; *Blatta* spp.;

Orthoptera: Acrididae; Gryllotalpidae;

Aphaniptera: *Pulex irritans;*

Anoplura: *Pediculus humanus;*

Isoptera: Termitidae;

Acarina: Tetranychidae.

The arthropod pests comtrolling composition of the present invention comprises the compound of the present invention and an inert carrier.

Generally, it is a formulation obtained by mixing the compound of the present invention, and a solid carrier, a liquid carrier, a gaseous carrier and/or bait(base material for poision bait) and the like, if necessary, adding a surfactant and other adjuvant for formulation. The formulation includes, for example, an oil solution, an emulsifiable concentrate, a flowable, a wettable powder, a granule, a dust, a microcapsule and the like. These formulation can be converted to use into a poison bait or a sheet. The arthropod pests controlling composition of the present invention is usually contained in an amount of 0.01 to 95% by weight of the compound of the present invention.

The solid carrier for formulation includes, for example, a fine power and a granule of clays (kaolin clay, diatomite, bentonite, Fubasami clay, acid clay, etc.), synthetic hydrated siliconoxide, talc, ceramic, other inorganic minerals (sericite, quartz, sulfur, activated carbon, calcium carbonate, etc.) or chemical fertilizers (ammonium sulfate, ammonium nitrate, ammonium chloride, etc.). The liquid carrier includes, for example, water, alcohols (methanol, ethanol, 2-propanol, ethylene glycol, etc.), ketones (acetone, methyl ethyl ketone, methyl isobutyl ketone, cyclohexanone, etc.), aromatic hydrocarbons (toluene, xylene, ethylbenzen, methylnaphthalene, etc.), aliphatic hydrocarbons (hexane, cyclohexane, kerosine, light oil, etc.), esters (ethyl acetate, butyl acetate, etc.), nitriles (acetonitrile, isobutyronitrile, etc.), ethers (ethylene glycol dimethyl ether, diisopropyl ether, 1,4-dioxane, tetrahydrofuran, etc.), acid amides (N,N-dimethylformamide, N,N-dimethylacetamide, etc.), halogenated hydrocarbons (dichloromethane, trichloroethane, etc.), dimethylsulfoxide and vegetable oils (soy bean oil, cotton seed oil, etc.).

The gaseous carrier includes, for example, fluorocarbons, butane gas, LPG (liquefied petroleum gas), dimethyl ether and carbon dioxide.

The surfactant includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, sticking agents, dispersing agents and stabilizing agents, and specifically for example, casein, gelatin, polysaccharides (starch, gum arabic, cellulose derivatives, alginic acid, etc.), lignin derivatives, synthetic water-soluble polymers (polyvinyl alcohol, polyvinylpyrrolidone, polyacrylic acid, etc.), PAP (isopropyl acid phosphate), BHT (2,6-di-t-butyl-4-methylphenol), BHA (a mixture of 2-t-butyl-4-methoxyphenol and 3-t-butyl-4-methoxyphenol), mineral oils, fatty acids, and fatty acid esters.

A base material for the poison bait includes, for example, bait ingredients such as grain powders, vegetable oils, sugars, and crystalline cellulose. The poison bait may be added, if necessary, antioxidants such as dibutylhydroxytoluene and nordihydroguaiaretic acid, preservatives such as dehydroacetic acid, agents for preventing from erroneously eating such as hot pepper powder, and pest-attractive flavors such as cheese flavor, onion flavor and peanut oil.

The arthropod pests controlling composition of the present invention is used by applying the arthropod pests controlling composition to pests directly and/or habitats of pests (nest, plant, soil, etc.). In the case of controlling the arthropod pest which is parasitic on a cultivating plant, for example, the arthropod pests controlling composition of the present invention is sprayed onto the upper side of the cultivating plant, pouring into the vicinities of a root of the cultivation plant and the like.

When the arthropod pests controlling composition of the present invention is used for a control of arthropod pests in agriculture and forestry, the application amount is usually 0.1 to 10,000 g as the compound of the present invention per 1,000 $m^2$. In case of the arthropod pests controlling composition of the present invention are formulated to emulsifiable concentrates, flowables, wettable powders and microcapsules, they are usually applied by spraying after dilution with water to have the concentration of the compound of the present invention to 10 to 10,000 ppm. In case of the arthropod pests controlling composition of the present invention are formulated to oil solutions, dusts and granules, they are usually applied as such.

When the arthropod pests controlling composition of the present invention is used for a control of epidemic, the application amount is usually 0.001 to 100 mg as the compound of the present invention per 1 m 2 in case of application for plane surface, and 0.001 to 10 mg as the compound of the present invention per 1 $m^3$ in case of application for open space. In the case of the arthropod pests controlling composition of the present invention are formulated to emulsifiable concentrates, flowables, wettable powders and microcapsules, they are usually applied after dilution with water to have the concentration of the compound of the present invention to 0.01 to 100,000 ppm. In case of the arthropod pests controlling composition of the present invention are formulated to oil solutions, aerosols, smoking agents and poison baits are usually applied as such.

The arthropod pests controlling composition of the present invention can also be used with other insecticides, nematocides, acaricides, fungicides, herbicides, plant growth regulators, synergists, fertilizers, soil conditioners, animal feeds, and the like.

Such insecticides and acaricides include, for example, organophosphorus compounds such as fenitrothion, fenthion, pyridaphenthion, diazinon, chlorpyrifos, chlorpyrifos-methyl, acephate, methidathion, disulfoton, DDVP, sulprofos, profenofos, cyanophos, dioxabenzofos, dimethoate, phenthoate, malathion, trichlorfon, azinphos-methyl, monocrotophos, dicrotophos, ethion, and fosthiazate;

carbamate compounds such as BPMC, benfuracarb, propoxur, carbosulfan, carbaryl, methomyl, ethiofencarb, aldicarb, oxamyl, fenothiocarb, and thiodicarb;

pyrethroid compounds such as etofenprox, fenvalerate, esfenvalerate, fenpropathrin, cypermethrin, alfa-cypermethrin, zeta-cypermethrin, permethrin, cyhalothrin, lambda-cyhalothrin, cyfluthrin, beta-cyfluthrin, deltamethrin, cycloprothrin, tau-fluvalinate, flucythrinate, bifenthrin, acrinathrin, tralomethrin, silafluofen, and halfenprox; neonicotinoid compounds such as acetamiprid, thiamethoxam, and thiacloprid; benzoylphenylurea compounds such as chlorfluazuron, teflubenzuron, flufenoxuron, and lufenuron; benzoylhydrazide compounds such as tebufenozide, halofenozide, methoxyfenozide and chromafenozide; thiadiazine derivatives such as buprofezin; nereistoxin derivatives such as cartap, thiocyclam, and bensultap; chlorinated hydrocarbon compounds such as endosulfan, gamma-BHC, and 1,1-bis(chlorophenyl)-2,2,2-trichloroethanol; formamidine derivatives such as amitraz and chlordimeform; thiourea derivatives such as diafenthiuron; phenylpyrazole derivatives such as ethiprole, and acetoprole; chlorfenapyr; pymetrozine; spinosad; indoxacarb; bromopropylate; tetradifon; chinomethionat; propargite; fenbutatin oxide; hexythiazox; etoxazole; clofentezine; pyridaben; pyridalyl; fenpyroximate; tebufenpyrad; pyrimidifen; fenazaquin; acequinocyl; bifenazate; fluacrypyrim; spirodiclofen; spiromesifen; milbemectin; avermectin; emamectin benzoate; azadirachtin; polynactin complexes such as tetranactin, idinactin, and trinactin; and the like.

The present invention will be further illustrated by the following production examples, formulation examples and test examples and the like; however, the present invention is not limited to these examples. In the following production examples, the data of $^1$H-NMR were measured in a solvent of deuterium chloroform with tetramethylsilane as the internal standard.

Production examples of the compound of the present invention are exemplified.

PRODUCTION EXAMPLE 1

To 2 g of N,N-dimethylformamide, 0.257 g of 5-chloro-3-(4-methylbenzyl)thio-1,2,4-thiadiazole and 0.145 g of 2,2-dimethyl-1,3-dioxolane-4-methanol were dissolved, and added 48 mg of sodium hydride (60% in oil) at about 0° C., followed by stirring at about 0° C. for 30 minutes and at room temperature for 4 hours. Then, the reaction mixture was added to saturated sodium chloride aqueous solution, and extracted with tert-butylmethylether. The organic layer was concentrated, and the residue obtaind was subjected to silica gel column chromatography to obtain 0.27 g of 5-(2,2-dimethyl-1,3-dioxolane-4-yl)methoxy-3-(4-methylbenzyl)thio-1,2,4-thiadiazole.

5-(2,2-dimethyl-1,3-dioxolane-4-yl)methoxy-3-(4-methylbenzyl)thio-1,2,4-thiadiazole (Which is Reffered to as the Compound of the Present Invention 1 Hereinafter)

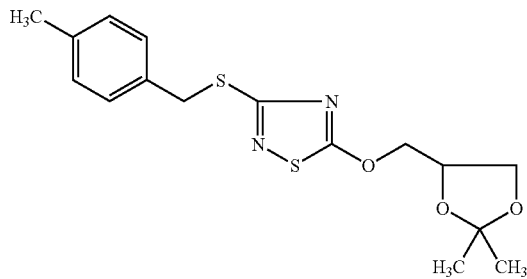

$^1$H-NMR: 7.29 (d, 2H) 7.11 (d, 2H) 4.54-4.44 (m, 3H) 4.37 (d, 2H) 4.15-4.11 (m, 1H) 3.83-3.80 (m, 1H) 2.32 (s, 3H) 1.45 (s, 3H) 1.38 (s, 3H)

PRODUCTION EXAMPLE 2

To 2 g of N,N-dimethylformamide, 312 mg of crude product of 5-chloro-3-(3,4-dichlorobenzyl)thio-1,2,4-thiadiazole which was produced by Reference Production Example 8 desbribed below and 0.145 g of 2,2-dimethyl-1,3-dioxolane-4-methanol were dissolved, and added 48 mg of sodium hydride (60% in oil) at about 0° C., followed by stirring at about 0° C. for 30 minutes and at room temperature for 4 hours. Then, the reaction mixture was added to saturated sodium chloride aqueous solution, and extracted with tert-butylmethylether. The organic layer was concentrated, and the residue obtaind was subjected to silica gel column chromatography to obtain 120 mg of 5-(2,2-dimethyl-1,3-dioxolane-4-yl)methoxy-3-(3,4-dichlorobenzyl)thio-1,2,4-thiadiazole.

5-(2,2-dimethyl-1,3-dioxolane-4-yl)methoxy-3-(3,4-dichlorobenzyl)thio-1,2,4-thiadiazole (Which is Reffered to as the Compound of the Present Invention 2 Hereinafter)

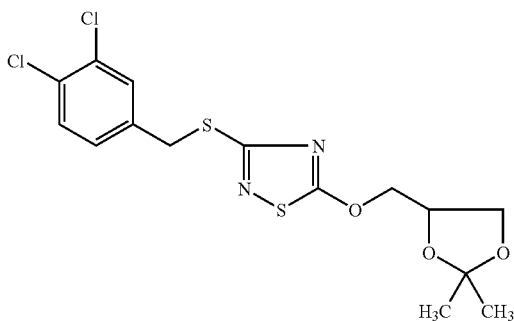

$^1$H-NMR: 7.55 (s, 1H) 7.36 (d, 1H) 7.26-7.22 (m, 1H) 4.55-4.44 (m, 3H) 4.31 (s, 2H) 4.15-4.09 (m, 1H) 3.84-3.80 (m, 1H) 1.45 (s, 3H) 1.38 (s, 3H)

PRODUCTION EXAMPLE 3

To 40 ml of N,N-dimethylformamide, 3.34 g of 5-chloro-3-methylthio-1,2,4-thiadiazole which was produced by Reference Production Example 1 desbribed below and 2.90 g of 2,2-dimethyl-1,3-dioxolane-4-methanol were dissolved, and added 880 mg of sodium hydride (60% in oil) at about 0° C., followed by stirring at same temperature for 1 hour. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 4.67 g of 5-(2,2-dimethyl-1,3-dioxolane-4-yl)methoxy-3-methylthio-1,2,4-thiadiazole.

5-(2,2-dimethyl-1,3-dioxolane-4-yl)methoxy-3-methylthio-1,2,4-thiadiazole (Which is Reffered to as the Compound of the Present Invention 3 Hereinafter)

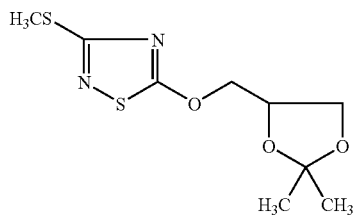

$^1$H-NMR: 4.57-4.46 (m, 3H) 4.16-4.09 (m, 1H) 3.85-3.81 (m, 1H) 2.60 (s, 3H) 1.45 (s, 3H) 1.35 (s, 3H)

PRODUCTION EXAMPLE 4

To 2 ml of N,N-dimethylformamide, 300 mg of crude product of 5-chloro-3-(3-chlorobenzyl)thio-1,2,4-thiadiazole which was produced by Reference Production Example 6 desbribed below and 157 mg of 2,2-dimethyl-1,3-dioxolane-4-methanol were dissolved, and added 52 mg of sodium hydride (60% in oil), followed by stirring at room temperature for 2 hours. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 150 mg of 5-(2,2-dimethyl-1,3-dioxolane-4-yl)methoxy-3-(3-chlorobenzyl)thio-1,2,4-thiadiazole.

5-(2,2-dimethyl-1,3-dioxolane-4-yl)methoxy-3-(3-chlorobenzyl)thio-1,2,4-thiadiazole (Which is Reffered to as the Compound of the Present Invention 4 Hereinafter)

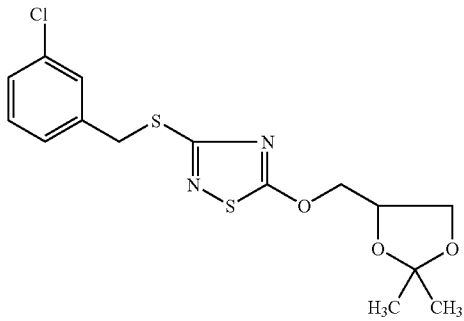

$^1$H-NMR: 7.42 (s, 1H) 7.31-7.22 (m, 2H) 4.54-4.45 (m, 3H) 4.35 (s, 2H) 4.16-4.11 (m, 1H) 3.85-3.81 (m, 1H) 1.45 (s, 3H) 1.38 (s, 3H)

PRODUCTION EXAMPLE 5

To 2 ml of N,N-dimethylformamide, 300 mg of crude product of 5-chloro-3-(2-chlorobenzyl) thio-1,2,4-thiadiazole which was produced by Reference Production Example 5 desbribed below and 157 mg of 2,2-dimethyl-1,3-dioxolane-4-methanol were dissolved, and added 52 mg of sodium hydride (60% in oil), followed by stirring at room temperature for 2 hours. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 140 mg of 5-(2,2-dimethyl-1,3-dioxolane-4-yl)methoxy-3-(2-chlorobenzyl)thio-1,2,4-thiadiazole.

5-(2,2-dimethyl-1,3-dioxolane-4-yl)methoxy-3-(2-chlorobenzyl)thio-1,2,4-thiadiazole (Which is Reffered to as the Compound of the Present Invention 5 Hereinafter)

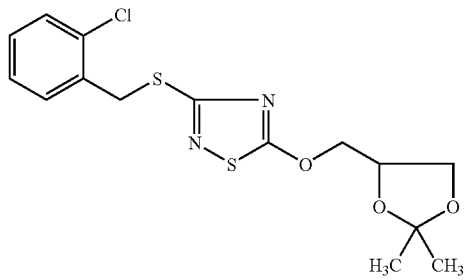

$^1$H-NMR: 7.56 (m, 1H) 7.37 (m, 1H) 7.20 (m, 2H) 4.56-4.45 (m, 5H) 4.15-4.11 (m, 1H) 3.84-3.80 (m, 1H) 1.45 (s, 3H) 1.38 (s, 3H)

PRODUCTION EXAMPLE 6

To 2 ml of N,N-dimethylformamide, 200 mg of 5-chloro-3-(4-methoxybenzyl)thio-1,2,4-thiadiazole which was produced by Reference Production Example 4 desbribed below and 153 mg of 2,2-dimethyl-1,3-dioxolane-4-methanol were dissolved, and added 35 mg of sodium hydride (60% in oil) at about 0° C., followed by stirring at about 0° C. for 15 minutes and at room temperature for 2 hours. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 200 mg of 5-(2,2-dimethyl-1,3-dioxolane-4-yl)methoxy-3-(4-methoxybenzyl)thio-1,2,4-thiadiazole.

5-(2,2-dimethyl-1,3-dioxolane-4-yl)methoxy-3-(4-methoxybenzyl)thio-1,2,4-thiadiazole (Which is Reffered to as the Compound of the Present Invention 6 Hereinafter)

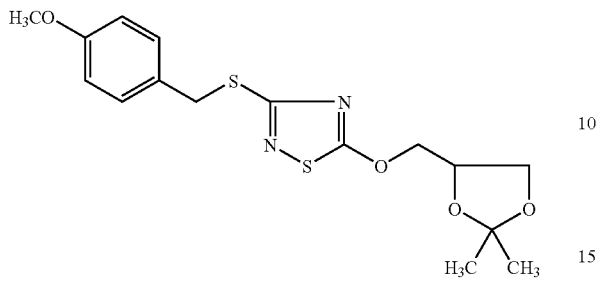

¹H-NMR: 7.33 (d, 2H) 6.84 (d, 2H) 4.54-4.46 (m, 3H) 4.36 (s, 2H) 4.15-4.13 (m, 1H) 3.84-3.79 (m, 4H) 1.45 (s, 3H) 1.38 (s, 3H)

PRODUCTION EXAMPLE 7

To 3 ml of N,N-dimethylformamide, 416 mg of crude product of 5-chloro-3-(4-chlorobenzyl)thio-1,2,4-thiadiazole which was produced by Reference Production Example 3 desbribed below and 198 mg of 2,2-dimethyl-1,3-dioxolane-4-methanol were dissolved, and added 72 mg of sodium hydride (60% in oil) at about 0° C., followed by stirring at same temperature for about 1 hour. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 460 mg of 5-(2,2-dimethyl-1,3-dioxolane-4-yl)methoxy-3-(4-chlorobenzyl)thio-1,2,4-thiadiazole.

5-(2,2-dimethyl-1,3-dioxolane-4-yl)methoxy-3-(4-chlorobenzyl)thio-1,2,4-thiadiazole (Which is Reffered to as the Compound of the Present Invention 7 Hereinafter)

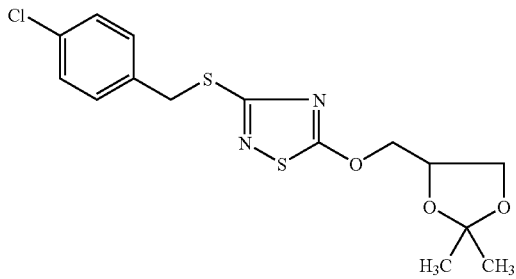

¹H-NMR: 7.36 (d, 2H) 7.27 (d, 2H) 4.55-4.44 (m, 2H) 4.35 (s, 2H) 4.17-4.10 (m, 1H) 3.84-3.81 (s, 1H) 1.47 (s, 3H) 1.38 (s, 3H)

PRODUCTION EXAMPLE 8

To 5 ml of N,N-dimethylformamide, 340 mg of 5-chloro-3-benzylthio-1,2,4-thiadiazole which was produced by Reference Production Example 2 desbribed below and 222 mg of 2,2-dimethyl-1,3-dioxolane-4-methanol were dissolved, and added 84 mg of sodium hydride (60% in oil) at about 0° C., followed by stirring at room temperature for about 1 hour. Then, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 370 mg of 5-(2,2-dimethyl-1,3-dioxolane-4-yl)methoxy-3-benzylthio-1,2,4-thiadiazole.

5-(2,2-dimethyl-1,3-dioxolane-4-yl)methoxy-3-benzylthio-1,2,4-thiadiazole (Which is Reffered to as the Compound of the Present Invention 8 Hereinafter)

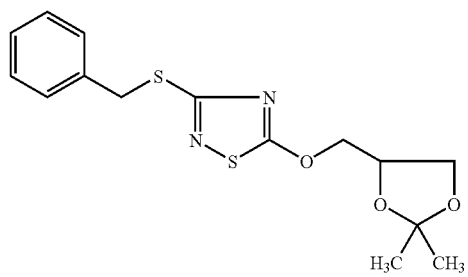

¹H-NMR: 7.42 (d, 2H) 7.34-7.24 (m, 3H) 4.55-4.43 (m, 3H) 4.40 (s, 2H) 4.15-4.12 (m, 1H) 3.84-3.81 (m, 1H) 1.45 (s, 3H) 1.35 (s, 3H)

PRODUCTION EXAMPLE 9

To 4 g of N,N-dimethylformamide, 386 mg of 5-chloro-3-allylthio-1,2,4-thiadiazole which was produced by Reference Production Example 10 desbribed below and 277 mg of 2,2-dimethyl-1,3-dioxolane-4-methanol were dissolved, and added 88 mg of sodium hydride (60% in oil) under ice cooling. After the mixture was stirred under ice cooling for 1 hour, the reaction mixture was added to saturated sodium chloride aqueous solution, and extracted with tert-butylmethylether. The organic layer was dried by anhydrous sodium sulfate, and the concentrated residue obtaind was subjected to silica gel column chromatography to obtain 530 mg of 5-(2,2-dimethyl-1,3-dioxolane-4-yl)methoxy-3-allylthio-1,2,4-thiadiazole.

5-(2,2-dimethyl-1,3-dioxolane-4-yl)methoxy-3-allylthio-1,2,4-thiadiazole (Which is Reffered to as the Compound of the Present Invention 9 Hereinafter)

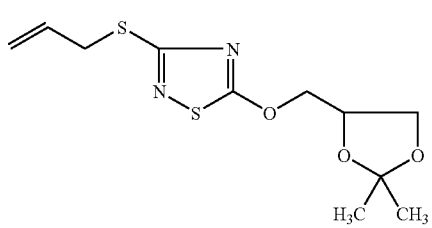

¹H-NMR: 5.96 (m, 1H) 5.32 (d, 1H) 5.15 (d, 1H) 4.51 (m, 3H) 4.13 (m, 1H) 3.84 (m, 3H) 1.45 (s, 3H) 1.36 (s, 3H)

PRODUCTION EXAMPLE 10

To 4 ml of N,N-dimethylformamide, 362 mg of 5-chloro-3-ethylthio-1,2,4-thiadiazole which was produced by Reference Production Example 7 desbribed below and 264 mg of 2,2-dimethyl-1,3-dioxolane-4-methanol were dissolved, and added 88 mg of sodium hydride (60% in oil) at about 0° C., followed by stirring at same temperature for 30 minutes. Then, the reaction mixture was added to saturated sodium chloride aqueous solution, and extracted with tert-butylmethylether. The organic layer was dried by anhydrous sodium sulfate, and the concentrated residue obtain was subjected to silica gel column chromatography to obtain 410 mg of 5-(2,2-dimethyl-1,3-dioxolane-4-yl)methoxy-3-ethylthio-1,2,4-thiadiazole.

5-(2,2-dimethyl-1,3-dioxolane-4-yl)methoxy-3-ethylthio-1,2,4-thiadiazole (Which is Reffered to as the Compound of the Present Invention 10 Hereinafter)

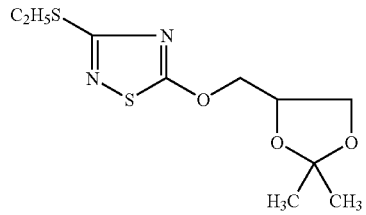

$^1$H-NMR: 4.51 (m, 3H) 4.14 (m, 1H) 3.84 (m, 1H) 3.17 (q, 2H) 1.41 (m, 9H)

PRODUCTION EXAMPLE 11

To 2 g of N,N-dimethylformamide, 0.243 g of 5-chloro-3-benzylthio-1,2,4-thiadiazole and 0.098 g of 3-furanmethanol were dissolved, and added 0.045 g of sodium hydride (60% in oil) at about 0° C., followed by stirring at about 0° C. for 1 hour and at room temperature for 2 hours. Then, the reaction mixture was added to saturated sodium chloride aqueous solution, and extracted with tert-butylmethylether. The organic layer was concentrated, and the residue obtain was subjected to silica gel column chromatography to obtain 0.17 g of 5-(3-furyl)methoxy-3-benzylthio-1,2,4-thiadiazole.

5-(3-furyl)methoxy-3-benzylthio-1,2,4-thiadiazole (Which is Reffered to as the Compound of the Present Invention 11 Hereinafter)

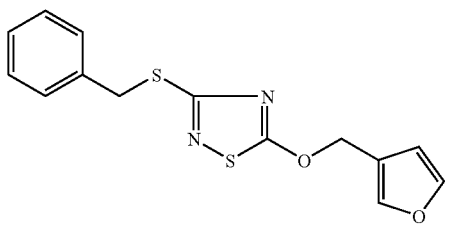

$^1$H-NMR: 7.56 (s, 1H) 7.42 (m, 3H) 7.30 (m, 3H) 6.50 (s, 1H) 5.37 (s, 2H) 4.41 (s, 2H)

PRODUCTION EXAMPLE 12

To 4 ml of N,N-dimethylformamide, 0.334 g of 5-chloro-3-methylthio-1,2,4-thiadiazole and 0.196 g of 2-furanmethanol were dissolved, and added 0.084 g of sodium hydride (60% in oil) at about 0° C., followed by stirring at about 0° C. for 0.5 hours and at room temperature for 4 hours. Then, the reaction mixture was added to saturated sodium chloride aqueous solution, and extracted with tert-butylmethylether. The organic layer was concentrated, and the residue obtain was subjected to silica gel column chromatography to obtain 0.25 g of 5-(2-furyl)methoxy-3-methylthio-1,2,4-thiadiazole.

5-(2-furyl)methoxy-3-methylthio-1,2,4-thiadiazole (Which is Reffered to as the Compound of the Present Invention 12 Hereinafter)

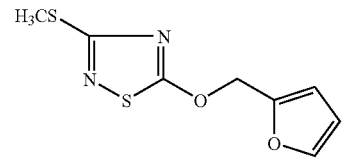

$^1$H-NMR: 7.47 (m, 1H) 6.56 (m, 1H) 6.40 (m, 1H) 5.45 (s, 2H) 2.62 (s, 3H)

PRODUCTION EXAMPLE 13

By using 0.196 g of 3-furanmethanol instead of 2-furanmethanol according to Production Example 12 was obtained 390 mg of 5-(3-furyl)methoxy-3-methylthio-1,2,4-thiadiazole. 5-(3-furyl)methoxy-3-methylthio-1,2,4-thiadiazole (which is reffered to as the compound of the present invention 13 hereinafter)

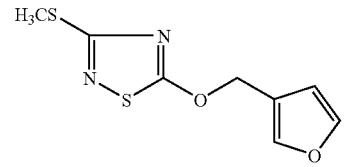

$^1$H-NMR: 7.58 (s, 1H) 7.43 (d, 1H) 6.51 (d, 1H) 5.38 (s, 2H) 2.62 (s, 3H)

PRODUCTION EXAMPLE 14

By using 204 mg of tetrahydro-3-furaemethanol instead of 2-furanmethanol according to Production Example 12 was obtained 406 mg of 5-(tetrahydro-3-furyl)methoxy-3-methylthio-1,2,4-thiadiazole.

5-(tetrahydro-3-furyl)methoxy-3-methylthio-1,2,4-thiadiazole (Which is Reffered to as the Compound of the Present Invention 14 Hereinafter)

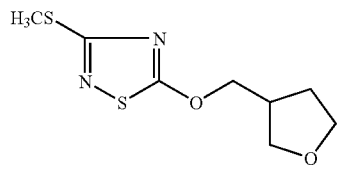

¹H-NMR: 4.49-4.36 (m, 2H) 3.93-3.65 (m, 4H) 2.84-2.74 (m, 1H) 2.60 (s, 3H) 2.17-2.05 (m, 1H) 1.76-1.65 (m, 1H)

PRODUCTION EXAMPLE 15

To 10 ml of N,N-dimethylformamide, 835 mg of 3-methylthio-5-chloro-1,2,4-thiadiazole and 520 mg of glycerol formal were dissolved, and added 204 mg of sodium hydride (60% in oil) at about 0° C., followed by stirring at about 0° C. for 20 minutes and at room temperature for 30 minutes. Then, the reaction mixture was added to saturated sodium chloride aqueous solution, and extracted with tert-butylmethylether. After the organic layer was dried by anhyrous sodium salfate, the organic layer was concentrated, and the residue obtaind was subjected to silica gel column chromatography (hexane:ethyl acetate=20:1), followed preparative HPLC to obtain 250 mg of 5-(1,3-dioxolane-4-yl)methoxy-3-methylthio-1,2,4-thiadiazole.

5-(1,3-dioxolane-4-yl)methoxy-3-methylthio-1,2,4-thiadiazole (Which is Reffered to as the Compound of the Present Invention 15 Hereinafter)

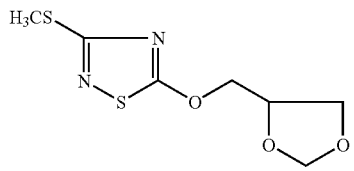

¹H-NMR: 5.08 (s, 1H) 4.93 (s, 1H) 4.55-4.45 (m, 3H) 4.06-4.02 (m, 1H) 3.82-3.78 (m, 1H) 2.60 (s, 3H)

PRODUCTION EXAMPLE 16

To 4 ml of N,N-dimethylformamide, 0.334 g of 5-chloro-3-methylthio-1,2,4-thiadiazole and 228 mg of 2-thiophenemethanol were dissolved, and added 0.084 g of sodium hydride (60% in oil) at about 0° C., followed by stirring at about 0° C. for 0.5 hours and at room temperature for 4 hours. Then, the reaction mixture was added to saturated sodium chloride aqueous solution, and extracted with tert-butylmethylether. The organic layer was concentrated, and the residue obtaind was subjected to silica gel column chromatography to obtain 66 mg of 5-(2-thienyl)methoxy-3-methylthio-1,2,4-thiadiazole.

5-(2-thienyl)methoxy-3-methylthio-1,2,4-thiadiazole (Which is Reffered to as the Compound of the Present Invention 16 Hereinafter)

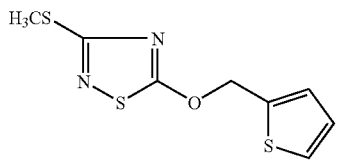

¹H-NMR: 7.38 (d, 1H) 7.25 (d, 1H) 7.22 (m, 1H) 5.65 (s, 2H) 2.62 (s, 3H)

PRODUCTION EXAMPLE 17

To 4 ml of N,N-dimethylformamide, 0.334 g of 5-chloro-3-methylthio-1,2,4-thiadiazole and 228 mg of 3-thiophenemethanol were dissolved, and added 0.084 g of sodium hydride (60% in oil) at about 0° C., followed by stirring at about 0° C. for 0.5 hours and at room temperature for 4 hours. Then, the reaction mixture was added to saturated sodium chloride aqueous solution, and extracted with tert-butylmethylether. The organic layer was concentrated, and the residue obtaind was subjected to silica gel column chromatography to obtain 500 mg of 5-(3-thienyl)methoxy-3-methylthio-1,2,4-thiadiazole.

5-(3-thienyl)methoxy-3-methylthio-1,2,4-thiadiazole (Which is Reffered to as the Compound of the Present Invention 17 Hereinafter)

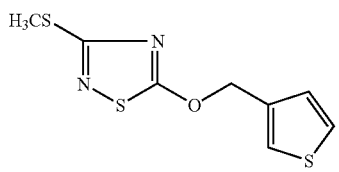

¹H-NMR: 7.43 (m, 1H) 7.35 (m, 1H) 7.17 (m, 1H) 5.49 (s, 2H) 2.61 (s, 3H)

PRODUCTION EXAMPLE 18

(1) To 90 ml of chloroform, 4.67 g of 5-(2,2-dimethyl-1,3-dioxolane-4-yl)methoxy-3-methylthio-1,2,4-thiadiazole was dissolved, and added 3.92 g of 3-chloroperoxybenzoic acid (purity 70%) which was devided to small portions at about 0° C., followed by stirring. Then, the reaction mixture was added to saturated sodium sulfite aqueous solution, and extracted with chloroform. The organic layer was successively washed with saturated sodium bicarbonate aqueous solution, saturated sodium chloride aqueous solution, dried by anhyrous sodium salfate, and concentrated. The residue was subjected to silica gel column chromatography to obtain 3.87 g of 5-(2,2-dimethyl-1,3-dioxolane-4-yl)methoxy-3-methaneslufinyl-1,2,4-thiadiazole.

5-(2,2-dimethyl-1,3-dioxolane-4-yl)methoxy-3-methaneslufinyl-1,2,4-thiadiazole

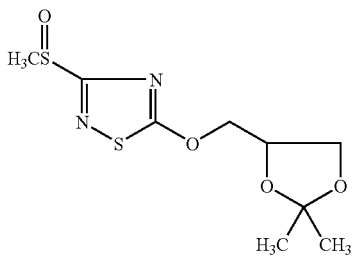

¹H-NMR: 4.67-4.49 (m, 3H) 4.18-4.14 (m, 1H) 3.86-3.32 (m, 1H) 2.30 (s, 3H) 1.46 (s, 3H) 1.39 (s, 3H)

(2) 2.97 g of 2,6-lutidine, 11.3 g of acetic anhydride and 4.38 g of trifluoroacetic anhydride were added to 3.87 g of 5-(2,2-dimethyl-1,3-dioxolane-4-yl)methoxy-3-methaneslufinyl 1,2,4-thiadiazole and mixed at about 0° C., followed by standing at room temperature for 3 days. Then, after the reaction mixture was concentrated under reduced pressure. The residue was added to saturated sodium bicarbonate aqueous solution, and extracted with tert-butylmethylether. The organic layer was concentrated, and the residue obtaind was subjected to silica gel column chromatography to obtain 0.18 g of 5-(2,2-dimethyl-1,3-dioxolane-4-yl)methoxy-3-(acetyloxymethyl)thio-1,2,4-thiadiazole.

5-(2,2-dimethyl-1,3-dioxolane-4-yl)methoxy-3-(acetyloxymethyl)thio-1,2,4-thiadiazole (Which is Reffered to as the Compound of the Present Invention 18 Hereinafter)

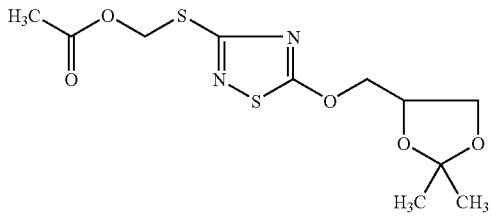

¹H-NMR: 5.75 (s, 2H) 4.57-4.47 (m, 3H) 4.17-4.13 (m, 1H) 3.85-3.82 (m, 1H) 2.11 (s, 3H) 1.45 (s, 3H) 1.39 (s, 3H)

PRODUCTION EXAMPLE 19

(1) To 4 ml of chloroform, 370 mg of 5-(2,2-dimethyl-1,3-dioxolane-4-yl)methoxy-3-benzylthio-1,2,4-thiadiazole was dissolved, and added 269 mg of 3-chloroperoxybenzoic acid (purity 70%) which was devided to small portions under ice cooling, followed by stirring. Then, the reaction mixture was added to saturated sodium sulfite aqueous solution, and extracted with chloroform. The organic layer was successively washed with saturated sodium bicarbonate aqueous solution, saturated sodium chloride aqueous solution, dried by anhyrous sodium salfate, and concentrated. The residue was subjected to silica gel column chromatography to obtain 360 mg of 5-(2,2-dimethyl-1,3-dioxolane-4-yl)methoxy-3-phenylslufinyl-1,2,4-thiadiazole.

5-(2,2-dimethyl-1,3-dioxolane-4-yl)methoxy-3-phenylslufinyl-1,2,4-thiadiazole

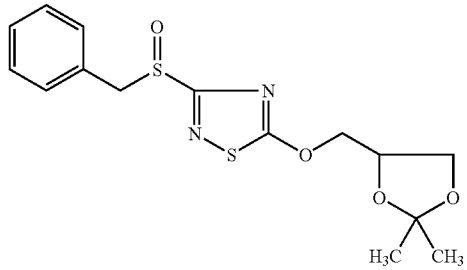

¹H-NMR: 7.33-7.19 (m, 5H) 4.66-4.48 (m, 3H) 4.42 (d, 1H) 4.34 (d, 1H) 4.18-4.14 (m, 1H) 3.86-3.82 (m, 1H) 1.47 (s, 3H) 1.40 (s, 3H)

(2) To 80 g of 5-(2,2-dimethyl-1,3-dioxolane-4-yl)methoxy-3-phenylslufinyl-1,2,4-thiadiazole, 100 mg of sodium acetate and 2 ml of acetic anhydride were added and mixed at 0° C., followed by refluxing for 14 hours. Then, the reaction mixture was added to saturated sodium bicarbonate aqueous solution, and extracted with tert-butylmethylether. The organic layer was concentrated, and the residue obtain was subjected to silica gel column chromatography to obtain 28 mg of 5-(2,2-dimethyl-1,3-dioxolane-4-yl)methoxy-3-(α-acetyloxybenzyl)thio-1,2,4-thiadiazole.

5-(2,2-dimethyl-1,3-dioxolane-4-yl)methoxy-3-(α-acetyloxybenzyl)thio-1,2,4-thiadiazole (Which is Reffered to as the Compound of the Present Invention 19 Hereinafter)

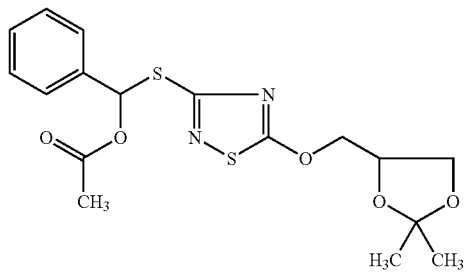

¹H-NMR: 7.74-7.73 (m, 1H) 7.53-7.51 (m, 2H) 7.41-7.35 (m, 3H) 4.58-4.32 (m, 3H) 4.20-4.07 (m, 1H) 3.86-3.73 (m, 1H) 2.10 (s, 3H) 1.46 (s, 3H) 1.39 (s, 3H)

PRODUCTION EXAMPLE 20

To 3 g of N,N-dimethylformamide, 468 mg of crude product of 5-chloro-3-(3,5-dichlorobenzyl)thio-1,2,4-thiadiazole which was produced by Reference Production Example 11 desbribed below and 198 mg of 2,2-dimethyl-1,3-dioxolane-4-methanol were dissolved, and added 42 mg of sodium hydride (60% in oil) at about 0° C., followed by stirring for 30 minutes. Then, to the reaction mixture, t-butylmethylether and saturated sodium chloride aqueous solution were added, and separeted to two layers. The organic layer was dried by anhyrous sodium salfate, and concentrated. The residue obtaind was subjected to column chromatography to obtain 72 mg of 5-(2,2-dimethyl-1,3-dioxolane-4-yl)methoxy-3-(3,5-dichlorobenzyl)thio-1,2,4-thiadiazole.

5-(2,2-dimethyl-1,3-dioxolane-4-yl)methoxy-3-(3,5-dichlorobenzyl)thio-1,2,4-thiadiazole (Which is Reffered to as the Compound of the Present Invention 20 Hereinafter)

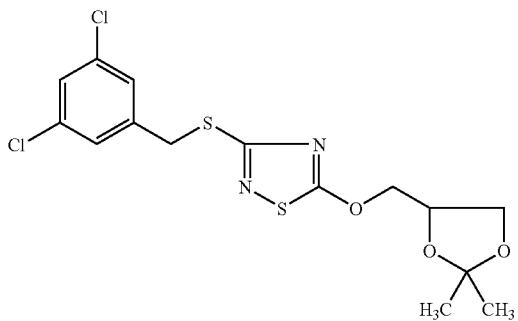

¹H-NMR: 7.32 (s, 2H) 7.24 (s, 1H) 4.54-4.43 (m, 3H) 4.30 (s, 2H) 4.15-4.11 (m, 1H) 3.84-3.81 (m, 1H) 1.48 (s, 3H) 1.41 (s, 3H)

PRODUCTION EXAMPLE 21

To 2 g of N,N-dimethylformamide, 300 mg of 5-chloro-3-(3-trifluoromethylbenzyl)thio-1,2,4-thiadiazole which was produced by Reference Production Example 12 desbribed below and 127 mg of 2,2-dimethyl-1,3-dioxolane-4-methanol were dissolved, and added 42 mg of sodium hydride (60% in oil) at about 0° C., followed by stirring at about 0° C. for 30 minutes and at room tempareture for 2 hours. Then, to the reaction mixture, t-butylmethylether and saturated sodium chloride aqueous solution were added, and separeted to two layers. The organic layer was dried by anhydrous sodium salfate, and concentrated. The residue obtain was subjected to column chromatography to obtain 370 mg of 5-(2,2-dimethyl-1,3-dioxolane-4-yl)methoxy-3-(3-trifluoromethylbenzyl)thio-1,2,4-thiadiazole.

5-(2,2-dimethyl-1,3-dioxolane-4-yl)methoxy-3-(3-trifluoromethylbenzyl)thio-1,2,4-thiadiazole (Which is Reffered to as the Compound of the Present Invention 21 Hereinafter)

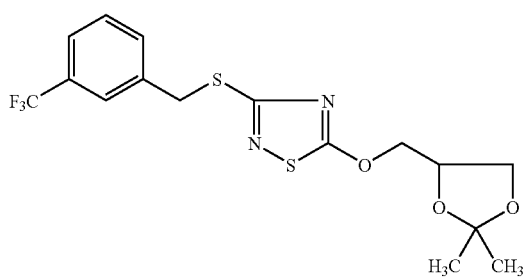

¹H-NMR: 7.69 (s, 1H) 7.61 (d, 1H) 7.50 (d, 1H) 7.42 (t, 1H) 4.55-4.42 (m, 5H) 4.15-4.11 (m, 1H) 3.84-3.81 (m, 1H) 1.45 (s, 3H) 1.38 (s, 3H)

PRODUCTION EXAMPLE 22

To 3 g of N,N-dimethylformamide, 300 mg of 5-chloro-3-ethoxymethylthio-1,2,4-thiadiazole and 188 mg of 2,2-dimethyl-1,3-dioxolane-4-methanol were dissolved, and added 62 mg of sodium hydride (60% in oil) at about 0° C., followed by stirring at about 0° C. for 30 minutes and standing at room tempareture for about 1 day. Then, to the reaction mixture, t-butylmethylether and saturated sodium chloride aqueous solution were added, and separeted to two layers. The organic layer was dried by anhydrous sodium salfate, and concentrated. The residue obtain was subjected to column chromatography to obtain 330 mg of 5-(2,2-dimethyl-1,3-dioxolane-4-yl)methoxy-3-ethoxymethylthio-1,2,4-thiadiazole.

5-(2,2-dimethyl-1,3-dioxolane-4-yl)methoxy-3-ethoxymethylthio-1,2,4-thiadiazole (Which is Reffered to as the Compound of the Present Invention 22 Hereinafter)

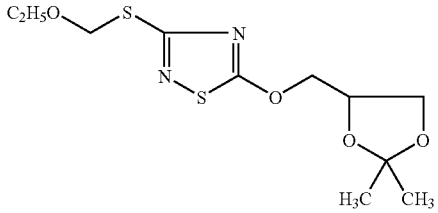

¹H-NMR: 5.39 (s, 2H) 4.58-4.47 (m, 3H) 4.16-4.11 (m, 1H) 3.86-3.82 (m, 1H) 3.68-3.63 (q, 2H) 1.45 (s, 3H) 1.39 (s, 3H) 1.23 (t, 3H)

PRODUCTION EXAMPLE 23

To 3 g of N,N-dimethylformamide, 350 mg of 5-chloro-3-benzyloxymethylthio-1,2,4-thiadiazole and 169 mg of 2,2-dimethyl-1,3-dioxolane-4-methanol were dissolved, and added 56 mg of sodium hydride (60% in oil) at about 0° C., followed by stirring at same tempareture for 2 hours. Then, to the reaction mixture, t-butylmethylether and saturated sodium chloride aqueous solution were added, and separeted to two layers. The organic layer was dried by anhydrous sodium salfate, and concentrated. The residue obtain was subjected to column chromatography to obtain 330 mg of 5-(2,2-dimethyl-1,3-dioxolane-4-yl)methoxy-3-benzyloxymethylthio-1,2,4-thiadiazole.

5-(2,2-dimethyl-1,3-dioxolane-4-yl)methoxy-3-benzyloxymethylthio-1,2,4-thiadiazole (Which is Reffered to as the Compound of the Present Invention 23 Hereinafter)

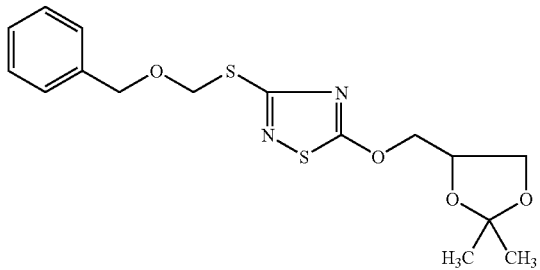

$^1$H-NMR: 7.36-7.28 (m, 5H) 5.41 (s, 2H) 4.69 (s, 2H) 4.57-4.46 (m, 3H) 4.16-4.11 (m, 1H) 3.85-3.82 (m, 1H) 1.45 (s, 3H) 1.39 (s, 3H)

Next, the production of the 5-chloro-1,2,4-thiadiazole compound which is the intermediate of the compound of the present invention is described as Reference Production Examples.

REFERENCE PRODUCTION EXAMPLE 1

To 100 ml of water, 18.7 g of methylisothiourea sulfate, 25 g of perchloromethylmercaptan, 0.15 g of sodiumdodecyl sulfate were added, followed the solution of 21 g of sodium hydroxide dissolved to 100 ml of water was added dropwise over a period for about 4 hours at about 0° C. After completion of addition, the mixture was stirred at same tempareture for 2 hours. Then, t-butylmethylether was added to the reaction mixture, and extracted. The organic layer was concentrated. The residue obtaind was distilled under reduced pressure, followed by subjecting to silica gel column chromatography (hexane:ethyl acetate=25:1) to obtain 7.64 g of 3-methylthio-5-chloro-1,2,4-thiadiazole.

3-methylthio-5-chloro-1,2,4-thiadiazole

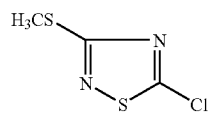

$^1$H-NMR: 2.66 (s, 3H)

REFERENCE PRODUCTION EXAMPLE 2

To the mixture of 20 ml of toluene and 10 ml of water, 2.02 g of benzylisothiourea hydrochloride, 1.86 g of perchloromethylmercaptan and 46 mg of benzyltriethylammonium chloride were added, followed the solution of 1.6 g of sodium hydroxide dissolved to 10 ml of water was added dropwise at about 0° C., and then stirred for 2 hours. Then, t-butylmethylether was added to the reaction mixture, and extracted. The organic layer was dried by anhydrous sodium salfate, and concentrated The residue obtaind was subjected to silica gel column chromatography (hexane:ethylacetate=20:1) to obtain 900 mg of 3-benzylthio-5-chloro-1,2,4-thiadiazole.

3-benzylthio-5-chloro-1,2,4-thiadiazole

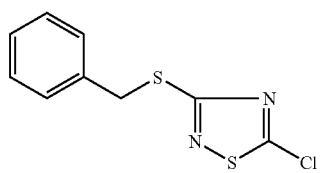

$^1$H-NMR: 7.60-7.20 (m, 5H) 4.45 (s, 2H)

REFERENCE PRODUCTION EXAMPLE 3

To the mixture of 80 ml of toluene and 40 ml of water, 10.0 g of 4-chlorobenzylisothiourea hydrochloride, 7.85 g of perchloromethylmercaptan and 192 mg of benzyltriethylammonium chloride were added, followed the solution of 6.75 g of sodium hydroxide dissolved to 40 ml of water was added dropwise over a period for 3 hours at about 0° C. Then, t-butylmethylether was added to the reaction mixture, and extracted. The organic layer was dried by anhydrous sodium salfate, and concentrated. The residue obtaind was subjected to silica gel column chromatography to obtain 5.38 g of 3-(4-chlorobenzyl)thio-5-chloro-1,2,4-thiadiazole.

3-(4-chlorobenzyl)thio-5-chloro-1,2,4-thiadiazole

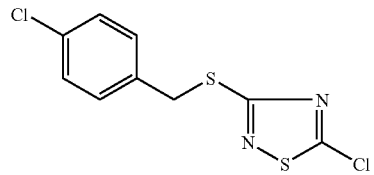

$^1$H-NMR: 7.37 (d, 2H) 7.27 (d, 2H) 4.40 (s, 2H)

REFERENCE PRODUCTION EXAMPLE 4

To the mixture of 20 ml of toluene and 10 ml of water, 2.53 g of 4-methoxybenzylisothiourea hydrochloride, 2.03 g of perchloromethylmercaptan and 50 mg of benzyltriethylammonium chloride were added, followed the solution of 1.74 g of sodium hydroxide dissolved to 10 ml of water was added dropwise over a period for 4 hours at about 0° C. After completion of addition, the mixture was stirred at room tempareture for 1 hour. Then, t-butylmethylether was added to the reaction mixture, and extracted. The organic layer was dried by anhydrous sodium salfate. The concentrated residue obtaind was subjected to silica gel column chromatography to obtain 5.38 g of 3-(4-methoxybenzyl)thio-5-chloro-1,2,4-thiadiazole.

3-(4-methoxybenzyl)thio-5-chloro-1,2,4-thiadiazole

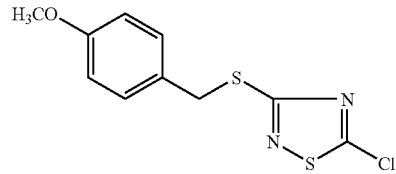

$^1$H-NMR: 7.35 (d, 2H) 6.85 (d, 2H) 4.41 (s, 2H) 3.79 (s, 3H)

REFERENCE PRODUCTION EXAMPLE 5

To the mixture of 80 ml of toluene and 40 ml of water, 10.0 g of 2-chlorobenzylisothiourea hydrochloride, 7.85 g of perchloromethylmercaptan and 192 mg of benzyltriethylammonium chloride were added, followed the solution of 5.27 g of sodium hydroxide dissolved to 40 ml of water was added dropwise over a period for 1 hour at about 0° C. Then, t-butylmethylether was added to the reaction mixture, and extracted. The organic layer was dried by anhydrous sodium salfate, and concentrated. The residue obtaind was subjected to silica gel column chromatography to obtain 0.78 g of 3-(2-chlorobenzyl)thio-5-chloro-1,2,4-thiadiazole.

3-(2-chlorobenzyl)thio-5-chloro-1,2,4-thiadiazole

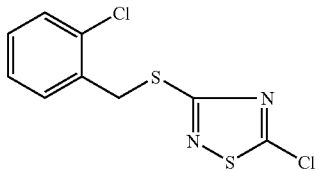

¹H-NMR: 7.55 (d, 1H) 7.49 (d, 1H) 7.22 (m, 2H) 4.57 (s, 2H)

REFERENCE PRODUCTION EXAMPLE 6

To the mixture of 80 ml of toluene and 40 ml of water, 10.0 g of 3-chlorobenzylisothiourea hydrochloride, 7.85 g of perchloromethylmercaptan and 192 mg of benzyltriethylammonium chloride were added, followed the solution of 5.27 g of sodium hydroxide dissolved to 40 ml of water was added dropwise over a period for 1 hour at about 0° C. Then, t-butylmethylether was added to the reaction mixture, and extracted. The organic layer was dried by anhydrous sodium salfate, and concentrated. The residue obtaind was subjected to silica gel column chromatography to obtain 1.30 g of 3-(3-chlorobenzyl)thio-5-chloro-1,2,4-thiadiazole.

3-(3-chlorobenzyl)thio-5-chloro-1,2,4-thiadiazole

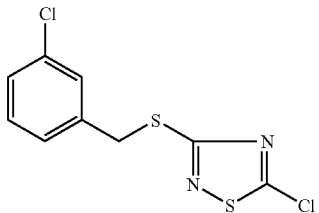

¹H-NMR: 7.43 (s, 1H) 7.31-7.22 (m, 3H) 4.41 (s, 2H)

REFERENCE PRODUCTION EXAMPLE 7

To 60 ml of water, 10.3 g of ehtylisothiourea hydrobromide, 10.4 g of perchloromethylmercaptan were added, followed the solution of 9.39 g of sodium hydroxide dissolved to 60 ml of water was added dropwise slowly at about 0° C. Then, t-butylmethylether was added to the reaction mixture, and extracted. The organic layer was dried by anhydrous sodium salfate, and concentrated. The residue obtaind was subjected to silica gel column chromatography (hexanne:ethylacetate=30:1) to obtain 2.54 g of 3-ethylthio-5-chloro-1,2,4-thiadiazole.

3-ethylthio-5-chloro-1,2,4-thiadiazole

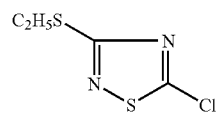

¹H-NMR: 3.22 (q, 2H) 1.44 (t, 3H)

REFERENCE PRODUCTION EXAMPLE 8

To 50 ml of water, 12.9 g of 3,4-dichlorobenzylisothiourea hydrochloride and 8.82 g of perchloromethylmercaptan were added, followed the solution of 7.58 g of sodium hydroxide dissolved to 50 ml of water was added dropwise slowly at about 0° C., followed by stirring for 4 hours. Then, t-butylmethylether was added to the reaction mixture, and extracted. The organic layer was dried by anhydrous sodium salfate, and concentrated. The residue obtaind was subjected to silica gel column chromatography to obtain 3.1 g of 3-(3,4-dichlorobenzyl)thio-5-chloro-1,2,4-thiadiazole as a crude product.

3-(3,4-dichlorobenzyl)thio-5-chloro-1,2,4-thiadiazole

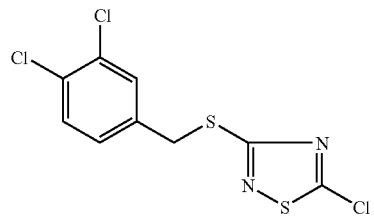

REFERENCE PRODUCTION EXAMPLE 9

To 50 ml of water, 9.46 g of 4-methylbenzylisothiourea hydrochloride and 8.11 g of perchloromethylmercaptan were added, followed the solution of 6.98 g of sodium hydroxide dissolved to 50 ml of water was added dropwise at about 0° C., followed by stirring for 4 hours. Then, t-butylmethylether was added to the reaction mixture, and extracted. The organic layer was dried by anhydrous sodium salfate, and concentrated. The residue obtaind was subjected to silica gel column chromatography to obtain 3.6 g of 3-(4-methylbenzyl)thio-5-chloro-1,2,4-thiadiazole as a crude product.

3-(4-methylbenzyl)thio-5-chloro-1,2,4-thiadiazole

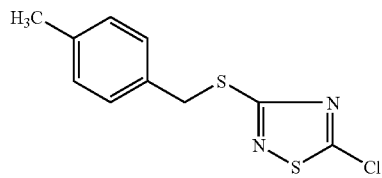

REFERENCE PRODUCTION EXAMPLE 10

To 50 ml of water, 9.33 g of allylisothiourea hydrochloride and 8.82 g of perchloromethylmercaptan were added, followed the solution of 7.58 g of sodium hydroxide dissolved to 50 ml of water was added dropwise at about 0° C., followed by stirring for 4 hours. Then, t-butylmethylether was added to the reaction mixture, and extracted. The organic layer was dried by anhydrous sodium salfate, and concentrated. The residue obtaind was subjected to silica gel column chromatography to obtain 3.6 g of 3-allylthio-5-chloro-1,2,4-thiadiazole.

3-allylthio-5-chloro-1,2,4-thiadiazole

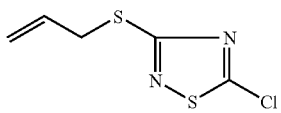

$^1$H-NMR: 6.03-5.83 (m, 1H) 5.34 (d, 1H) 5.19 (d, 1H) 3.88 (d, 1H)

REFERENCE PRODUCTION EXAMPLE 11

To the mixture of 25 ml of water and 25 ml of dichloromethane, 8.95 g of 3,5-dichlorobenzylisothiourea hydrochloride and 6.12 g of perchloromethylmercaptan were added, followed the solution of 5.26 g of sodium hydroxide dissolved to 50 ml of water was added dropwise at about 0° C. over the period for about 3 hours. After completion of addition, the mixture was stirred at room tempareture for 1 hour. Then, chloroform was added to the reaction mixture, and extracted. The organic layer was dried by anhydrous sodium salfate, and concentrated. The residue obtaind was subjected to silica gel column chromatography (hexane:ethylacetate=30:1) to obtain 2.4 g of crude 3-(3,5-dichlorobenzyl)thio-5-chloro-1,2,4-thiadiazole as a crude product.

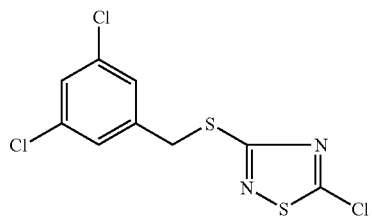

REFERENCE PRODUCTION EXAMPLE 12

To the mixture of 25 ml of water and 50 ml of dichloromethane, 12.0 g of 3-trifluoromethylbenzylisothiourea hydrochloride and 8.24 g of perchloromethylmercaptan were added, followed the solution of 7.09 g of sodium hydroxide dissolved to 25 ml of water was added dropwise at about 0° C. over the period for about 1.5 hours. After completion of addition, the mixture was stirred at room tempareture for 2 hours. Then, chloroform was added to the reaction mixture, and extracted. The organic layer was dried by anhydrous sodium salfate, and concentrated. The residue obtaind was subjected to silica gel column chromatography (hexane:ethylacetate=20:1) to obtain 5.9 g of 3-(3-trifluoromethylbenzyl)thio-5-chloro-1,2,4-thiadiazole.

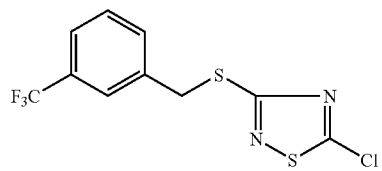

$^1$H-NMR: 7.69 (s, 1H) 7.61 (d, 1H) 7.52 (d, 1H) 7.44 (t, 1H) 4.47 (s, 2H)

REFERENCE PRODUCTION EXAMPLE 13

To the mixture of 35 ml of water and 70 ml of dichloromethane, 12.2 g of ethoxymethylisothiourea hydrochloride and 13.2 g of perchloromethylmercaptan were added, followed the solution of 11.4 g of sodium hydroxide dissolved to 35 ml of water was added dropwise at about 0° C. over the period for about 1.5 hours. After completion of addition, the mixture was stirred at room tempareture for 1 hour. Then, chloroform was added to the reaction mixture, and extracted. The organic layer was dried by anhydrous sodium salfate, and concentrated. The residue obtaind was subjected to silica gel column chromatography to obtain 5.22 g of 3-ethoxymethylthio-5-chloro-1,2,4-thiadiazole.

3-ethoxymethylthio-5-chloro-1,2,4-thiadiazole

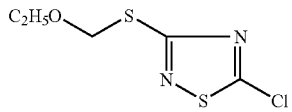

$^1$H-NMR: 5.43 (s, 2H) 3.68 (q, 2H) 1.26 (t, 3H)

REFERENCE PRODUCTION EXAMPLE 14

To the mixture of 25 ml of water and 50 ml of dichloromethane, 11.3 g of benzyloxymethylisothiourea hydrochloride and 9.02 g of perchloromethylmercaptan were added, followed the solution of 7.76 g of sodium hydroxide dissolved to 25 ml of water was added dropwise at about 0° C. over the period for about 1.5 hours. After completion of addition, the mixture was stirred at room tempareture for 1 hour. Then, chloroform was added to the reaction mixture, and extracted. The organic layer was dried by anhydrous sodium salfate, and concentrated. The residue obtaind was subjected to silica gel column chromatography to obtain 3.51 g of 3-benzyloxymethylthio-5-chloro-1,2,4-thiadiazole. 3-benzyloxymethylthio-5-chloro-1,2,4-thiadiazole

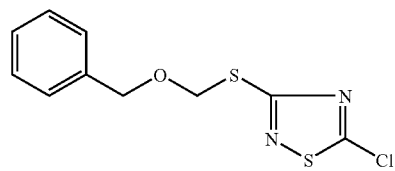

$^1$H-NMR: 7.36-7.28 (m, 5H) 5.45 (s, 2H) 4.69 (s, 2H)

Next, formulation examples will be described below. Parts represent parts by weight.

FORMULATION EXAMPLE 1

9 parts of each of the compounds of the present invention 1 to 23 is dissolved in 37.5 parts of xylene and 37.5 parts of N,N-dimethylformamide, and 10 parts of polyoxyethylene styryl phenyl ether and 6 parts of calcium dodecylbenzenesulfonate are added thereto, followed by well stirring and mixing, to give a emulsifiable concentrate for each compound.

FORMULATION EXAMPLE 2

9 parts of each of the compounds of the present invention 1 to 23 is added to a mixture containing 4 parts of sodium laurylsulfate, 2 parts of calcium lignin sulfonate, 20 parts of synthetic hydrated silicone oxide fine powder, and 65 parts of diatomaceous earth, followed by well stirring and mixing, to give a wettable powder for each compound.

FORMULATION EXAMPLE 3

To 3 parts of each of the compounds of the present invention 1 to 23 are added 5 part of synthetic hydrated silicon oxide fine powder, 5 parts of sodium dodecylbenzenesulfonate, 30 parts of bentonite, and 57 parts of clay, followed by well stirring and mixing, and an appropriate amount of water is added to this mixture, followed by further stirring, granulation with a granulator, and air drying, to give a granule for each compound.

FORMULATION EXAMPLE 4

4.5 parts of each of the compounds of the present invention 1 to 23, 1 part of synthetic hydrated silicon oxide fine powder, 1 part of DRILESS B (manufactured by Sankyo Co., Ltd.) as a coagulant and 7 parts of clay are mixed thoroughly in a mortar, then, stirred to mix by a juice mixer. To the resulted mixture is added 86.5 parts of cut clay, they were sufficiently stirred to mix, to obtain a dust for each compound.

FORMULATION EXAMPLE 5

10 parts of each of the compounds of the present invention 1 to 23, 35 parts of white carbon containing 50 parts of polyoxyethylene alkyl ether sulfate ammonium salt, and 55 parts of water are mixed and pulverized by the wet grinding method to give a formulation for each compound.

FORMULATION EXAMPLE 6

0.5 part of each of the compounds of the present invention 1 to 23 is dissolved in a 10 parts of dichloromethane, and the resulting solution is mixed with 89.5 parts of Isper M (isoparafin; trademark of Exxon Chemical) to give an oil solution for each compound.

FORMULATION EXAMPLE 7

An aerosol vessel is filled with 0.1 part of each of the compounds of the present invention 1 to 23 and 49.9 parts of Noethiozol (manufactured by Chuo Kasei Co.). Then, the vessel is equipped with an aerosol valve, 25 parts of dimethylether and 25 parts of liquefied petroleum gas are charged into the aerosol vessel is shaken and equipped with an actuator, to give an oil-based aerosol.

FORMULATION EXAMPLE 8

An aerosol vessel is filled with 0.6 part of each of the compounds of the present invention 1 to 23, 0.01 part of BHT, 5 parts of xylene, 3.39 parts of deodorized kerosene and 1 part of an emulsifiable agent (Atmos 300, trademark of Atmos Chemicals Co.), and 50 parts of water. Then, the vessel is equipped with a valve and 40 parts of a propellant (LPG) is charged through the valve into the aerosol vessel under pressure, to give a water-based aerosol.

Continuously, it is shown by a Test Example that the compound of the present invention is useful as an active ingredient of an arthropod pests controlling composition.

TEST EXAMPLE

Each formulation on the test compounds obtained according to the Formulation Example 5 was diluted with water so that the active ingredient concentration came to 500 ppm to prepare a diluting liquid.

The seeds of cucumber were planted in polyethylene cups and grown until their first foliage leaves developed, on which about 20 cotton aphids (*Aphis gossypii*) were made parasitic. After one day, the diluting liquid described above was sprayed at the rate of 20 ml/cup onto the cucumber plants. On 6 day after application, the number of cotton aphids (*Aphis gossypii*) was examined.

As a result, in the treatment of the compound of the present invention 1 to 9, 11, 13 to 15, 17 to 23, the numbers of the living cotton aphids (*Aphis gossypii*) were three or less. On the other hand, in the non-treatment, the number of the living cotton aphids (*Aphis gossypii*) was twenty or more.

INDUSTRIAL APPLICABILITY

By using the compound of the present invention, arthropod pests can be controlled.

The invention claimed is:

1. A thiadiazole compound of the formula (A):

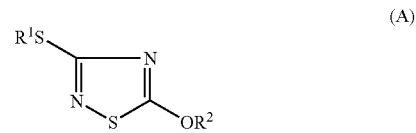

(A)

wherein, in the formula, $R^1$ represents a C1-C7 alkyl group, a C3-C7 alkenyl group, a C3-C7 alkynyl group, a C2-C7 alkoxyalkyl group, a C2-C7 alkylthioalkyl group, a C4-C7 alkoxyalkoxyalkyl group, a C4-C7 alkylthioalkoxyalkyl group, a phenyl group in which the phenyl group may be substituted, a C1-C2 alkyl group substituted with a phenyl group in which the phenyl group may be substituted, a C1-C2 alkyl group substituted with a phenoxy group in which the phenoxy group may be substituted, a C2-C3 alkoxyalkyl group substituted with a phenyl group in which the phenyl group may be substituted, or the formula (B):

(B)

wherein $R^3$ represents a C1-C3 alkyl group, $R^4$ represents a hydrogen atom, a methyl group, an ethyl group, a propyl group, or a phenyl group in which the phenyl group may be substituted; and $R^2$ represents a C1-C4 alkyl group substituted with a hetero ring group in which the hetero ring group may be substituted, which the hetero ring group is a five-membered ring containing only an oxygen atom(s) or a sulfur atom(s) as a hetero atom(s).

2. The thiadiazole compound according to claim 1, wherein $R^1$ is a C1-C7 alkyl group in the formula (A).

3. The thiadiazole compound according to claim 1, wherein $R^1$ is a C3-C7 alkenyl group, a C2-C7 alkoxyalkyl group, a C2-C7 alkylthioalkyl group, a C4-C7 alkoxyalkoxyalkyl group, or a C4-C7 alkylthioalkoxyalkyl group in the formula (A).

4. The thiadiazole compound according to claim 1, wherein $R^1$ is a phenyl group in which the phenyl group may be substituted with one or more selected from the Substituent Group A described below, a C1-C2 alkyl group substituted with a phenyl group in which the phenyl group may be substituted with one or more selected from the Substituent Group A described below, a C1-C2 alkyl group substituted with a phenyloxy group in which the phenyloxy group may be substituted with one or more selected from the Substituent Group A described below, or a C2-C3 alkoxyalkyl group substituted with a phenyl group in which the phenyl group may be substituted with one or more selected from the Substituent Group A described below in the formula (A);
Substituent Group A
C1-C4 alkyl group, C1-C4 haloalkyl group, C1-C4 alkoxy group, C1-C4 alkylthio group, C1-C4 haloalkoxy group, nitro group, cyano group, and halogen atoms.

5. The thiadiazole compound according to claim 1, wherein $R^1$ is the formula (B):

wherein $R^3$ represents a C1-C3 alkyl group, and $R^4$ represents a hydrogen atom, a methyl group, a ethyl group, or a phenyl group in which the phenyl group may be substituted with one or more selected from the group consisting of C1-C4 alkyl group, C1-C4 haloalkyl group, C1-C4 alkoxy group, C1-C4 alkylthio group, C1-C4 haloalkoxy group, nitro group, cyano group, and halogen atoms;
in the formula (A).

6. The thiadiazole compound according to claim 1, wherein $R^1$ is a phenyl group in which the phenyl group may be substituted with one or more selected from the Substituent Group A described below, a benzyl group in which the benzyl group may be substituted with one or more selected from the Substituent Group A described below, a phenyloxymethyl group in which the phenyloxymethyl group may be substituted with one or more selected from the Substituent Group A described below, or a benzyloxymethyl group in which the benzyloxymethyl group may be substituted with one or more selected from the Substituent Group A described below in the formula (A);
Substituent Group A
C1-C4 alkyl group, C1-C4 haloalkyl group, C1-C4 alkoxy group, C1-C4 alkylthio group, C1-C4 haloalkoxy group, nitro group, cyano group, and halogen atoms.

7. The thiadiazole compound according to claim 1, wherein $R^2$ is a C1-C4 alkyl group substituted with hetero ring group in which the hetero ring group may be substituted with one or more selected from the Substituent Group B described below, which the hetero ring group is a five-membered ring containing only an oxygen atom(s) or a sulfur atom(s) as a hetero atom(s) in the formula (A);
Substituent Group B
C1-C4 alkyl group, halogen atoms, trifluoromethyl group, formyl group, and nitro group.

8. The thiadiazole compound according to claim 1, wherein $R^2$ is a C1-C4 alkyl group substituted with hetero ring group in which the hetero ring group may be substituted with one or more selected from the Substituent Group B described below, which the hetero ring group is a five-membered ring containing only an oxygen atom(s) as a hetero atom(s) in the formula (A);
Group B
C1-C4 alkyl group, halogen atoms, trifluoromethyl group, formyl group, and nitro group.

9. A arthropod pests controlling composition comprising an effective amount of the thiadiazole compound according to claim 1.

10. A method for controlling arthropod pests comprising applying an effective amount of the thiadiazole compound according to claim 1 to arthropod pests or habitat for arthropod pests.

* * * * *